(12) United States Patent
Norton et al.

(10) Patent No.: US 11,026,674 B2
(45) Date of Patent: Jun. 8, 2021

(54) ANCHORING SYSTEM AND METHOD FOR SECURING A SUTURE TO A PRE-DRILLED HOLE

(71) Applicant: Biomet Manufacturing, LLC, Warsaw, IN (US)

(72) Inventors: Daniel R. Norton, Warsaw, IN (US); Jacy C. Hoeppner, Warsaw, IN (US); Jason D. Meridew, Warsaw, IN (US); Christopher M. Palese, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 179 days.

(21) Appl. No.: 16/414,352

(22) Filed: May 16, 2019

(65) Prior Publication Data

US 2019/0350577 A1    Nov. 21, 2019

Related U.S. Application Data

(60) Provisional application No. 62/673,667, filed on May 18, 2018.

(51) Int. Cl.
*A61B 17/04* (2006.01)
*A61F 2/08* (2006.01)

(52) U.S. Cl.
CPC ........ *A61B 17/0401* (2013.01); *A61F 2/0811* (2013.01); *A61B 2017/044* (2013.01);
(Continued)

(58) Field of Classification Search
CPC ........ A61B 17/0401; A61B 2017/0409; A61B 2017/0411; A61B 2017/044;
(Continued)

(56) References Cited

U.S. PATENT DOCUMENTS 9,131,937 B2 *   9/2015   Chan .................. A61B 17/0401
9,526,492 B2 *  12/2016   Lombardo ......... A61B 17/0469
(Continued)

FOREIGN PATENT DOCUMENTS

WO    2016172508    10/2016
WO    2017106608     6/2017

OTHER PUBLICATIONS

"European Application Serial No. 19175256.7, Extended European Search Report dated Jan. 3, 2020", 8 pgs.
(Continued)

*Primary Examiner* — Eric S Gibson

(74) *Attorney, Agent, or Firm* — Schwegman Lundberg & Woessner, P.A.

(57) ABSTRACT

An anchoring system can use an implant delivery device to deploy an implant into a pre-drilled bore, to secure one or more sutures between a threaded outer surface of an implant body and a wall of the bore. The implant delivery device can controllably rotate the implant about its longitudinal axis. The implant delivery device can include a projection extending distally from a distal end of an inner shaft. The implant delivery device can controllably translate a wire between a distally extended position, at which the wire can form a closed loop with the projection and a distal end of the inner shaft, and a proximally retracted position, at which the wire can be at least partially retracted into the distal end of the inner shaft.

20 Claims, 19 Drawing Sheets

(52) U.S. Cl.
CPC ............... *A61B 2017/0409* (2013.01); *A61B 2017/0445* (2013.01); *A61F 2002/0852* (2013.01); *A61F 2002/0888* (2013.01)

(58) Field of Classification Search
CPC .... A61B 2017/0441; A61B 2017/0443; A61B 2017/0445; A61F 2/0811; A61F 2002/0847; A61F 2002/0852; A61F 2002/0888
See application file for complete search history.

(56) References Cited

U.S. PATENT DOCUMENTS

| | | | | |
|---|---|---|---|---|
| 9,597,068 | B2* | 3/2017 | Sengun | A61B 17/0469 |
| 10,383,618 | B2* | 8/2019 | Gustafson | A61B 17/0485 |
| 10,463,357 | B2* | 11/2019 | Gustafson | A61B 17/0485 |
| 10,639,026 | B2* | 5/2020 | Gustafson | A61B 17/1604 |
| 10,820,915 | B2* | 11/2020 | Orphanos | A61B 17/1633 |
| 2001/0049529 | A1* | 12/2001 | Cachia | A61B 17/68 606/301 |
| 2009/0248068 | A1* | 10/2009 | Lombardo | A61B 17/0401 606/232 |
| 2010/0087857 | A1* | 4/2010 | Stone | A61B 17/0469 606/232 |
| 2013/0123842 | A1* | 5/2013 | Chan | A61B 17/0401 606/232 |
| 2014/0081325 | A1* | 3/2014 | Sengun | A61B 17/0401 606/232 |
| 2014/0277128 | A1* | 9/2014 | Moore | A61B 17/0642 606/232 |
| 2014/0277129 | A1* | 9/2014 | Arai | A61B 17/0401 606/232 |
| 2016/0135801 | A1* | 5/2016 | Lombardo | A61B 17/0469 606/232 |
| 2017/0172562 | A1* | 6/2017 | Lombardo | A61B 17/0401 |
| 2019/0059875 | A1* | 2/2019 | Srikumaran | A61B 50/20 |
| 2019/0350577 | A1* | 11/2019 | Norton | A61B 17/0401 |
| 2020/0337753 | A1* | 10/2020 | Braun | A61B 17/8635 |

OTHER PUBLICATIONS

"European Application Serial No. 19175256.7, Response filed Jul. 22, 2020 to Extended European Search Report dated Jan. 3, 2020", 15 pgs.

"European Application Serial No. 19175256.7, Communication Pursuant to Article 94(3) EPC dated Oct. 14, 2020", 3 pgs.

"European Application Serial No. 19175256.7, Response filed Apr. 26, 2021 to Communication Pursuant to Article 94(3) EPC dated Oct. 14, 2020", 107 pages.

* cited by examiner

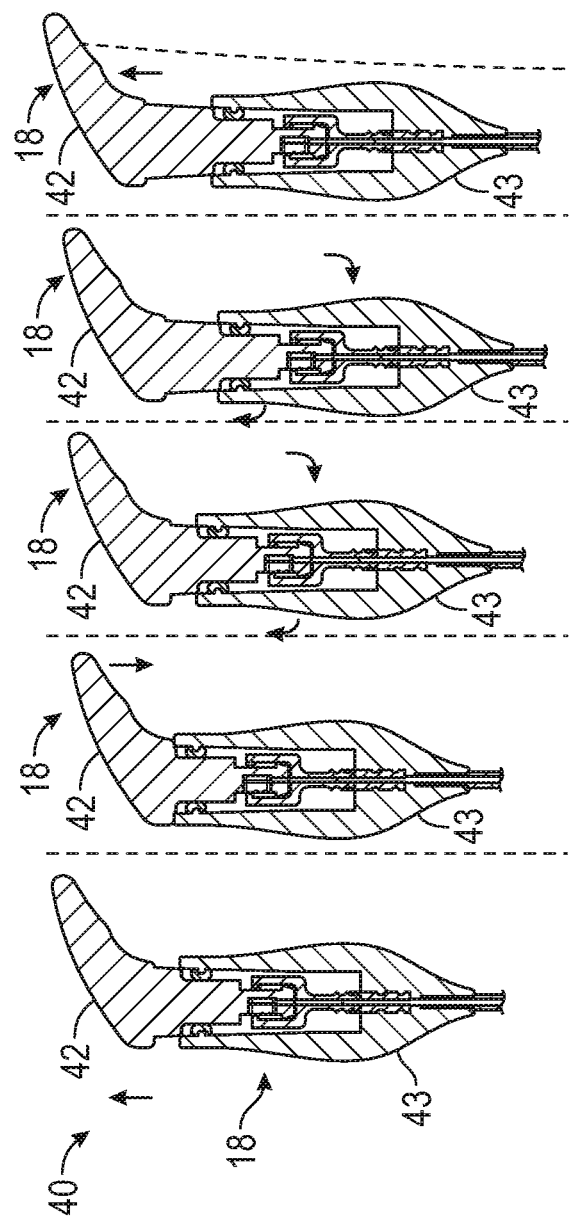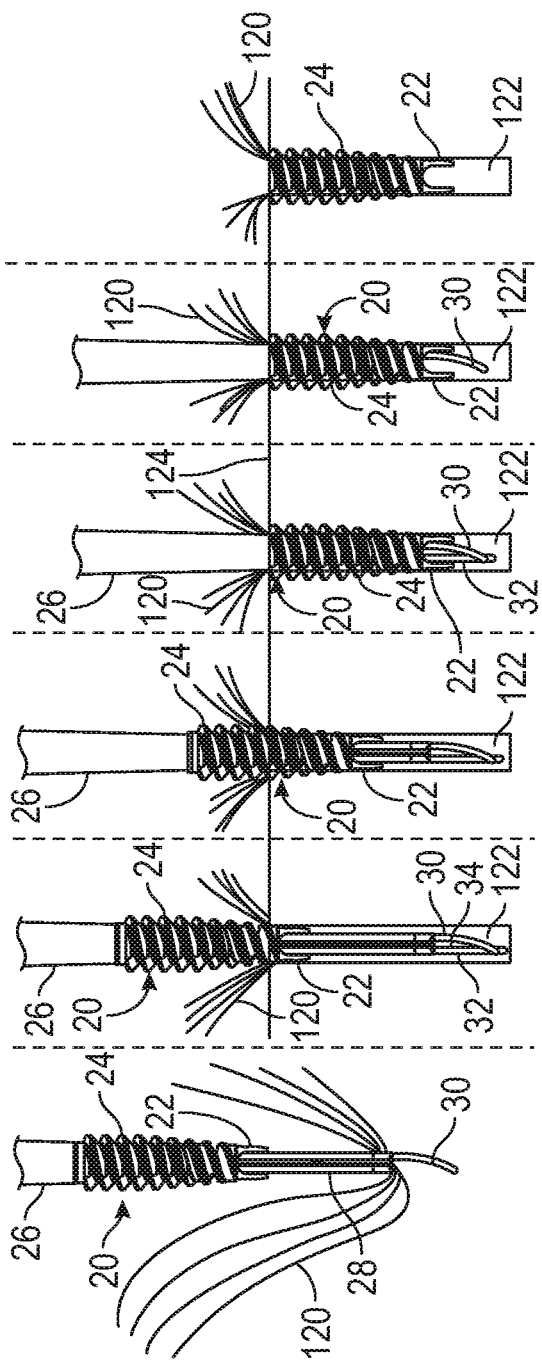

ANCHORING SYSTEM AND METHOD FOR SECURING A SUTURE TO A PRE-DRILLED HOLE

CLAIM OF PRIORITY

This application claims the benefit of U.S. Provisional Patent Application Ser. No. 62/673,667, filed on May 18, 2018, the benefit of priority which is claimed hereby, and is incorporated by reference herein in its entirety.

FIELD

The present disclosure relates to surgical implant systems, including implants, delivery instruments, and methods for installing the implants. Specifically, the present disclosure relates to an anchoring system including knotless implants, also referred to as suture anchors, for securing soft tissue to bone with the use of implant delivery devices.

BACKGROUND

The successful reattachment of soft tissue to bone can be a significant concern, especially in the sports medicine industry. Surgical or medical procedures are often performed on a body, for example, a human body or anatomy, to repair or replace various portions thereof. For example, the soft tissues of the body may need to be reattached to bones due to trauma, overuse, surgical intervention, or disease.

Soft tissue can be reattached to bone using devices such as screws, staples, and various types of suture anchors or tacks. In an example using suture anchors, a suture is passed through a selected portion of the soft tissue and the suture anchor is deployed into the bone such as into a pre-formed hole, which can require various different instruments and tying a knot to secure the suture to the anchor.

Overview

This disclosure pertains generally to systems, methods and devices that facilitate the rapid connection of sutures to tissue fixation implants such as a suture anchors. For example, the systems, methods and devices can facilitate the passage of one or more sutures through the implant and the connection of the one or more sutures to the implant with a minimal change in tension on the one or more sutures from prior to and after deployment of the implant into bone. In some examples, the one or more sutures can be cut during deployment of the implant into bone.

The present inventor has recognized, among other things, that existing soft tissue fixation solutions can require a multiple step process where connection of the suture to the implant can be challenging. This process can include deploying an implant into bone and connecting suture(s) to the deployed implant. It can often be difficult to accomplish such connection as the suture(s) must be knotted or otherwise connected while maintaining the suture at a desired amount of tension. Failure to provide adequate tension (providing too much or too little) can cause the suture(s) to be ineffective necessitating repetition of the entire process in some cases.

Considering these factors, the present inventors propose an anchoring device and related systems and methods that can reduce the number of currently used surgical processes to provide for faster, easier, and more reproducible surgical techniques. Thus, the present application discloses an anchor device configuration where once a desired degree of tension is provided to the suture, upon deployment of the anchor device, connection of the suture(s) to the anchor is accomplished and the desired tension is substantially maintained during this process. In some examples, the suture(s) can additionally be cut during deployment of the suture(s) anchor into bone, thereby reducing the number of additional steps required during the surgical process.

To further illustrate the apparatuses, systems and methods disclosed herein, the following non-limiting examples are provided:

In Example 1, an anchoring system includes an anchoring system, comprising: an implant delivery device, including: a handle, including an implant actuator handle portion including a grip, a driving portion, a ratchet portion, and a tip, wherein an actuating ratchet including a plurality of grooves is positioned within the ratchet portion; and a wire actuator handle portion including an inner surface defining a bore and a plurality of flexible arms extending from the inner surface toward a longitudinal axis of the wire actuator handle portion, wherein a number of the flexible arms are configured to engage the grooves of the ratchet portion as the implant actuator handle portion is rotated, the number of flexible arms is less than a total number of the plurality of flexible arms.

In Example 2, the Example 1 can optionally be configured such that the wire actuator handle portion is positioned distal to the grip.

In Example 3, any one or a combination of Examples 1-2 can optionally be configured such that the implant delivery device includes a distal end that is convertible from an open configuration to a closed configuration.

In Example 4, any one or a combination of Examples 1-3 can optionally be configured such that the wire actuator handle portion is configured to transition the distal end from the closed configuration to the open configuration by moving the wire actuator handle portion proximally relative to the implant actuator handle portion.

In Example 5, any one or a combination of Examples 1-4 can optionally be configured such that the implant delivery device further includes: a cannulated outer shaft non-rotationally coupled to the implant actuating handle portion.

In Example 6, any one or a combination of Examples 1-5 can optionally be configured to further include a cannulated implant non-rotationally coupled to a distal end of the cannulated outer shaft.

In Example 7, any one or a combination of Examples 1-6 can optionally be configured such that wherein, when a rotational force is applied to the grip, the rotational force is translated to the cannulated implant via the cannulated outer shaft.

In Example 8, any one or a combination of Examples 1-7 can optionally be configured such that wherein the rotational force is applied to the grip, the implant actuating handle portion rotates relative to the wire actuating handle portion.

In Example 9, an implant delivery device includes a cannulated outer shaft; an inner shaft slidably received in the cannulated outer shaft, a projection extending distally beyond a distal end of the inner shaft; a wire translatable through the inner shaft from a retracted position to an extended position, the extended position including a distal end of the wire extending a distance beyond the distal end of the inner shaft such that the wire and the projection form a closed loop for trapping a suture; and a handle, including: a wire actuator handle portion configured to controllably translate the wire from the extended position to the retracted position; and an implant actuator handle portion including a grip that is configured to controllably rotate the cannulated outer shaft, the grip positioned proximal to the wire actuator handle portion.

In Example 10, Examples 9 can optionally be configured such wherein the wire actuator handle portion includes an inner surface defining a bore and a plurality of flexible arms extending from the inner surface toward a longitudinal axis of the wire actuator portion In Example 11, any one or a combination of Examples 9 or 10 can optionally be configured such that wherein the implant delivery device further includes an actuating ratchet positioned within a ratchet portion of the implant actuator handle portion, the actuating ratchet including a plurality of grooves.

In Example 12, any one or a combination of Examples 9-11 can optionally be configured such that wherein the wire actuator handle portion is positioned around the ratchet portion of the implant actuator handle portion.

In Example 13, any one or a combination of Examples 9-12 can optionally be configured such that wherein the plurality of flexible arms are configured to engage a respective groove of the actuating ratchet.

In Example 14, any one or a combination of Examples 9-13 can optionally be configured such as the grip is rotated, the ratchet portion rotates within and relative to the wire actuating handle portion.

In Example 15, any one or a combination of Examples 9-14 can optionally be configured such that wherein, as the grip is rotated within the wire actuating handle portion, the plurality of flexible arms are configured such that less than all of the plurality of flexible arms engage the actuating ratchet.

In Example 16, any one or a combination of Examples 9-15 can optionally be configured such that the wire actuator handle portion is configured to move proximally relative to the implant actuator handle portion to retract the wire and transition the closed loop to an open loop.

In Example 17, any one or a combination of Examples 9-15 can optionally be configured such that the implant actuator handle portion is configured to rotate relative to the wire actuator handle portion to move a cannulated implant coupled to the cannulated outer shaft distally relative to the wire actuator handle portion In Example 18, a method includes securing a suture to a pre-drilled bore, the method comprising: providing an implant delivery device including a distal end and a handle portion, wherein the distal end is convertible from an open configuration to a closed configuration, and the handle includes: an implant actuator handle portion including a grip that is configured to controllably rotate the implant body; a wire actuator handle portion positioned around a portion of the implant actuator handle portion such that the wire actuator handle portion is positioned distal to the implant actuator handle portion, the wire actuator handle portion configured to controllably transition the distal end from a closed configuration to an open configuration; positioning the distal end of the implant delivery device, in the open configuration, proximate the suture; converting the distal end of the implant delivery device from the open configuration to the closed configuration to encircle the suture in an eyelet of the closed configuration, the suture being slidable through the eyelet when the distal end is in the closed configuration; inserting the distal end of the implant delivery device into the pre-drilled bore; deploying a cannulated implant, having a threaded outer surface, from the implant delivery device into the pre-drilled bore, the cannulated implant securing the suture between the threaded outer surface and a wall of the pre-drilled bore when the cannulated implant is deployed; and converting the distal end of the implant delivery device from the closed configuration to the open configuration; and retracting the implant delivery device from the pre-drilled bore.

In Example 19, Example 18 can optionally be configured such that deploying the cannulated implant comprises: controllably rotating the cannulated implant about a longitudinal implant axis of the cannulated implant.

In Example 20, any one or a combination of Examples 18 and 19 can optionally be configured such that wherein controllably rotating the cannulated implant about a longitudinal implant axis of the cannulated implant includes: imparting a rotation to the grip of the implant actuating handle portion that translates the rotation to a cannulated outer shaft of the implant delivery device and to the cannulated implant that is non-rotationally coupled to a distal end of the cannulated outer shaft; and wherein converting the distal end of the implant delivery device from the closed configuration to the open configuration includes: controllably moving the wire actuator handle portion proximally relative to the implant actuating device to retract a portion of a wire into the inner shaft.

This overview is intended to provide an overview of subject matter of this document. The overview discusses the inventive subject matter in a general, non-limiting, manner to provide an introduction to the more detailed description provided below in reference to the various figures included in this disclosure. It is not intended to provide an exclusive or exhaustive explanation of the invention. The detailed description is included to provide further information about the present document.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 12A illustrates a side cross-section of the handle and a side view of a distal end of the implant delivery device including the implant mounted to the implant delivery device where the wire actuator has been moved proximally relative to the implant actuator, according to some example embodiments.

FIG. 12B illustrates the side cross-section of the handle and the side view of a distal end of the implant delivery device shown in FIG. 12A where the wire actuator has moved distally relative to the implant actuator to capture the sutures and the implant delivery device is positioned within a bore, according to some example embodiments.

FIG. 12C illustrates the side cross-section of the handle and the side view of a distal end of the implant delivery device shown in FIGS. 12A-B where the implant actuator has been rotated relative to the wire actuator to advance the implant into the bore, according to some example embodiments.

FIG. 12D illustrates the side cross-section of the handle and the side view of a distal end of the implant delivery device shown in FIGS. 12A-C where the implant actuator has been rotated relative to the wire actuator to fully advance the implant into the bore such that a distal end of the implant is at least flush with a bone surface, according to some example embodiments.

FIG. 12E illustrates the side cross-section of the handle and the side view of a distal end of the implant delivery device shown in FIGS. 12A-D where the wire actuator has been moved proximally relative to the implant actuator to retract the wire to free the sutures from the implant delivery device, according to some example embodiments.

FIG. 12F illustrates where the implant delivery device shown in FIGS. 12A-E has been withdrawn from the implant, according to some example embodiments.

The present inventors propose an anchoring device and related systems and methods that can reduce the number of currently used surgical processes to provide for faster, easier, and more reproducible surgical techniques.

DETAILED DESCRIPTION

The present application relates to systems, methods and devices that facilitate the rapid connection of sutures to implants such as tissue fixation implants, e.g., a suture anchor, and deployment of the implants into pre-drilled bores. For example, the systems, methods and devices can facilitate the passage of one or more sutures through the implant (referred to herein as "suture anchor") and the connection of the one or more sutures to the implant with a minimal change in tension on the one or more sutures from prior to and after deployment of the implant into bone. The present implants have applicability to a variety of orthopedic procedures as well as to the sports medicine industry. Thus, the present implants are applicable to the repair of and/or fixation to various anatomical locations and features including, for example, the labrum of the shoulders and hips.

During a surgical process, such as a rotator cuff repair surgery, a surgeon can drill one or more bores in a bone. The surgeon can affix sutures to the bone at each bore. For each hole, the surgeon can deploy an implant (e.g., suture anchor) into the bore, which can secure the suture between the threads of the implant body and the wall of the bore. The device and method discussed herein pertain to the implant, the elements used in an implant delivery device that can deploy the implant, and a method of deploying the implant.

An anchoring system can use an implant delivery device to deploy the implant including an implant body and a distal member coupled to the implant body into a pre-drilled bore, to secure one or more sutures between a threaded outer surface of an implant body and a wall of the bore. The implant delivery device can controllably rotate the implant body about its longitudinal axis. The distal member is positioned distal to the implant body and is freely rotatable about the longitudinal axis relative to the implant body. The implant delivery device can include a projection extending distally from a distal end of an inner shaft. The delivery device can controllably translate a wire between a distally extended position, at which the wire can form a closed loop with the projection and a distal end of the inner shaft, and a proximally retracted position, at which the wire can be at least partially retracted into the distal end of the inner shaft and form an open loop.

Figure 1:
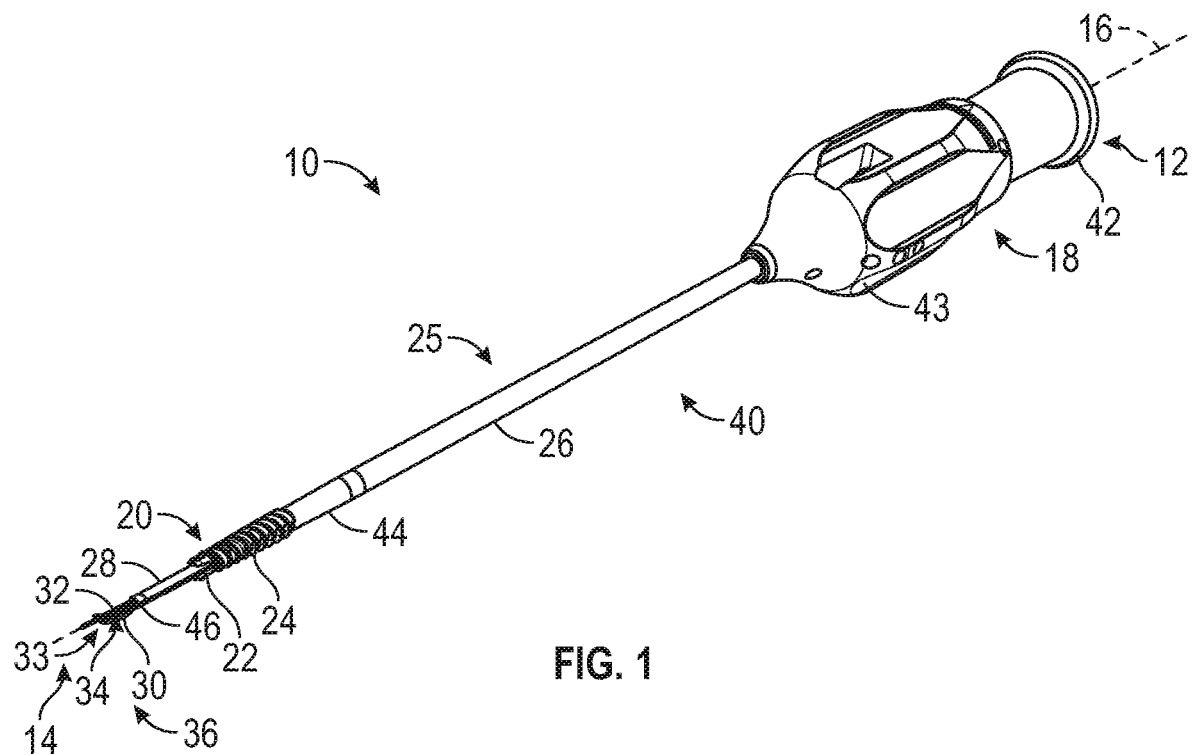
FIG. 1 illustrates a perspective view of a system for soft tissue repair including an implant delivery system and an implant, according to some example embodiments.

FIG. 1 illustrates a perspective view of an anchoring system 10 for repair of soft tissue. The system 10 includes an implant delivery device 40 and an implant 20. The implant delivery device 40 extends from a proximal end 12 to a distal end 14 and can be configured for facilitating fixation of the implant 20 into bone of a patient.

The implant delivery device 40 can deploy the implant 20 in a bore to secure sutures at the location of the bore. In some examples, the implant 20 can be pre-loaded onto the implant delivery device 40, and can be shipped with the implant delivery device 40. In other examples, a surgeon can load the implant 20 onto the implant delivery device 40, as needed.

The implant delivery device 40 can include a handle 18, a drive shaft 25 and a suture grasper 36. The drive shaft 25 can have at least two concentric elements including a cannulated outer shaft 26 and an inner shaft 28 extending along a longitudinal axis (16) of the implant delivery device 40. The cannulated outer shaft 26 is disposed around the inner shaft 28. As discussed herein, the cannulated outer shaft 26 and the inner shaft 28 are disposed over a wire 32.

One of the concentric elements can be rotated about a longitudinal axis 16 of the implant delivery device 40, with respect to another one of the concentric elements. In an example, when a surgeon initiates rotation at the handle 18, the cannulated outer shaft 26 can translate the rotation to a distal portion of the cannulated outer shaft 26 and can rotate an implant body 24 of the implant 20 that is mounted onto the distal portion of the cannulated outer shaft 26.

Figure 2:
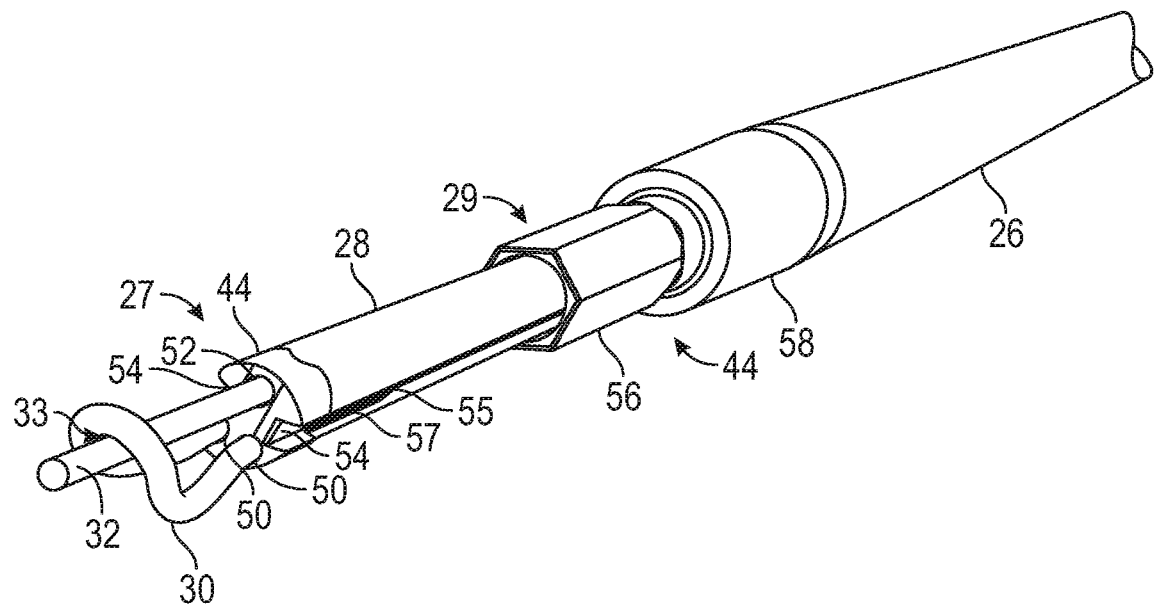
FIG. 2 illustrates a perspective view of a portion of the implant delivery system, according to some example embodiments.

As seen in FIG. 2, which illustrates the distal end 29 of the cannulated outer shaft 26 without the implant 20, includes an implant holder portion 44 that engages with the implant 20. The implant holder portion 44 can be formed integral with the cannulated outer shaft 26 or can be a separate element that can be rotationally coupled to the cannulated outer shaft 26. When a surgeon initiates a rotation at the handle 18, via implant actuator 43 (i.e., a distal handle portion), of the implant delivery device 40, the cannulated outer shaft 26 and the implant holder portion 44 can couple the rotation to the distal portion 29 of the cannulated outer shaft 29, and can rotate about the wire 32 and the inner shaft 28.

During a surgical procedure, the implant delivery device 40 can deploy the implant 20 (a cannulated implant). The implant 20 remains anchored in the bone after the procedure has been completed, while the implant delivery device 40 is removed. The implant 20 locks the sutures to the bore by trapping the sutures between external threads on the implant 20 and a wall of the bore. Prior to deployment, a portion of the implant 20 can be disposed over the distal portion 29 of the cannulated outer shaft 26 along the implant holder portion 44. The portion disposed over the distal portion 29 of the cannulated outer shaft 26 along the implant holder portion 44 is rotationally locked to the cannulated outer shaft 26 such that any rotation translated from the handle 18 to the cannulated outer shaft 26 will be translated to the portion of the implant 20 disposed along the implant holder portion 44.

The suture grasper 36 can include a projection 30 and a wire 32 that are configured to form an eyelet 34 (see FIG. 6; also referred to herein as a closed loop) that can be opened and closed, as discussed herein. The projection 30 extends distally from a distal end 27 of the inner shaft 28. The projection 30 can have a smaller cross-section than the inner shaft 28, when viewed end-on from a distal end of the system 10.

The projection 30 can be laterally offset from the longitudinal axis 16 of the implant delivery device 40. In some examples, the projection curves from a first lateral edge of the inner shaft 28 toward a second lateral edge of the inner shaft 28, opposite the first lateral edge. In some examples, the proximal and distal ends of the projection 30, extending from the inner shaft 28, are on opposite sides of the longitudinal axis 16 of the implant delivery device 40. That is, the projection 30 is bent (e.g., non-planar).

A wire 32 can be controllably translatable between a distally extended position, at which the wire 32 forms the eyelet 34 (a closed loop) with the projection 30 and a distal end 27 of the inner shaft 28, and a proximally retracted position, at which the wire 32 is at least partially retracted into the distal end 27 of the inner shaft 28 forming an open loop. In some examples, the wire 32 can extend parallel to the projection 30 at a proximal portion of the projection 30. The wire 32 can be shaped so that when the wire is fully extended distally, the wire 32 can contact a distal portion of the projection 30, and can form a closed loop from the wire 32, projection 30, and distal end 27 of the inner shaft 28. In some examples, the wire 32 can be formed as a rod, a tube, or other element having various cross-sectional shapes that can translate longitudinally. In some examples, the wire 32 can optionally include one or more slots, holes, or notches, which can increase the flexibility of the wire 32. The wire 32 can be formed from a metal, plastic, or another suitable material.

As discussed herein, the wire 32 contacts the projection 30 to form the closed loop that defines the eyelet 34 that one or more sutures can extend through. In one example, the projection 30 can include an opening 33 that can receive the wire 32. For example, the projection 30 can be a bent loop such that the opening 33 is aligned with the wire 32. When the wire 32 is inserted into the opening 33, the closed loop is formed to define the eyelet 34 that is configured to receive one or more flexible members or sutures. As discussed herein, instead of having to thread a suture through an eyelet, a surgeon can retract the wire 32, via the wire actuator 42 of the handle 18, such that the wire 32 moves toward the proximal end 16 of the implant delivery device 40 and forms an open loop. A surgeon can then place the suture across the projection 30 and subsequently move the wire 32 distally thereby forming a closed loop and enclosing the suture within the eyelet 34.

A surgeon can open or close the eyelet 34 by manipulating the handle 18, via the wire actuator 42. To do so, the surgeon can impart a longitudinal translation of the wire 32 from an element at the handle 18, e.g., the wire actuator 42. The surgeon can retract the wire 32 proximally (thereby opening the loop), or advance the wire 32 distally (thereby closing the loop). During a stage of surgery, a surgeon can open the loop (e.g., open the eyelet 34), position the implant delivery device 40 so that sutures extend across the projection 30 and close the eyelet 34. When the eyelet 34 is closed, the sutures pass through the eyelet 34. The surgeon can use this eyelet 34 to pull the sutures distally to a bottom of the bore of the patient, then can open the eyelet 34 and withdraw the implant delivery device 40 proximally. As discussed herein, a distal member 22 of the implant 20 can capture and hold the distal-most portions of the sutures in place when the inner shaft 28 and the projection 30 are withdrawn.

Prior to use, the implant delivery device 40 can have its loop either open or closed (e.g., can have the wire 32 retracted proximally or advanced distally). As a first stage during use, the surgeon can position the implant delivery device 40, with the loop open, to "grab" the relevant sutures in the loop. This positioning is performed outside the bone.

Referring to FIGS. 1, 2, 3, and 6, the inner shaft 28 can include a connector 46 positioned at a distal end 27 of the inner shaft 28 to couple the projection 30 to the inner shaft 28. For example, the connector 46 can include at least one opening 50 to receive a portion of the projection 30. In the example shown, the projection 30 is a bent loop and the connector 46 includes two openings 50 to receive the two free ends of the loop. However, other configurations are possible. For example, instead of a bent loop, the projection 30 can be, e.g., a curved plate including an opening to receive the second portion 32 or a non-planar projection that can contact the distal end of the wire 32. Additionally the number of openings 50 can vary and the connector 46 and the projection 30 can either be modular (as shown) or integral with each other and the inner shaft 28.

The connector 46 further includes an aperture 52 extending through the connector 46 that the wire 32 can pass through. As discussed herein, the wire 32 is coupled within and extends from the wire actuator 42 of the handle 18, through the cannulated outer shaft 26, the inner shaft 28, and the connector 46 and contacts the projection 30 to form the closed loop defining the eyelet 34.

Figure 3:
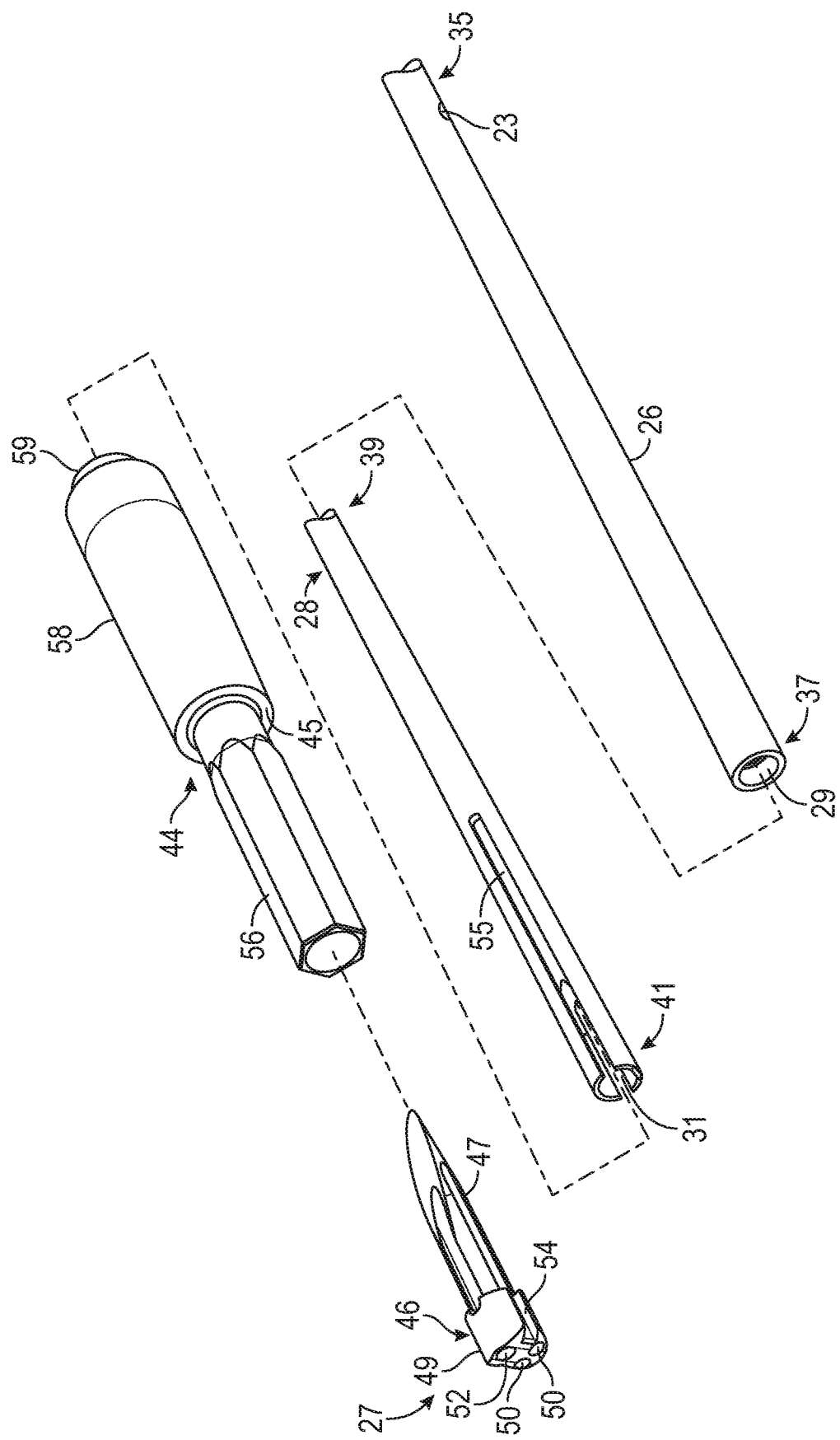
FIG. 3 illustrates an expanded view of a portion of the implant delivery system, according to some example embodiments.

The connector 46 is coupled to the inner shaft 28 that extends from the handle 18. Referring to FIGS. 2, 3, and 6, the connector 46 includes slots 54 and the inner shaft 28 includes slots 55 that cooperate to form an alignment slot 57. In one example, the connector 46 and the inner shaft 28 each include two slots 54, 55 that cooperate to form two alignment slots 57. However, the number of alignment slots 57 can vary.

Figure 9:
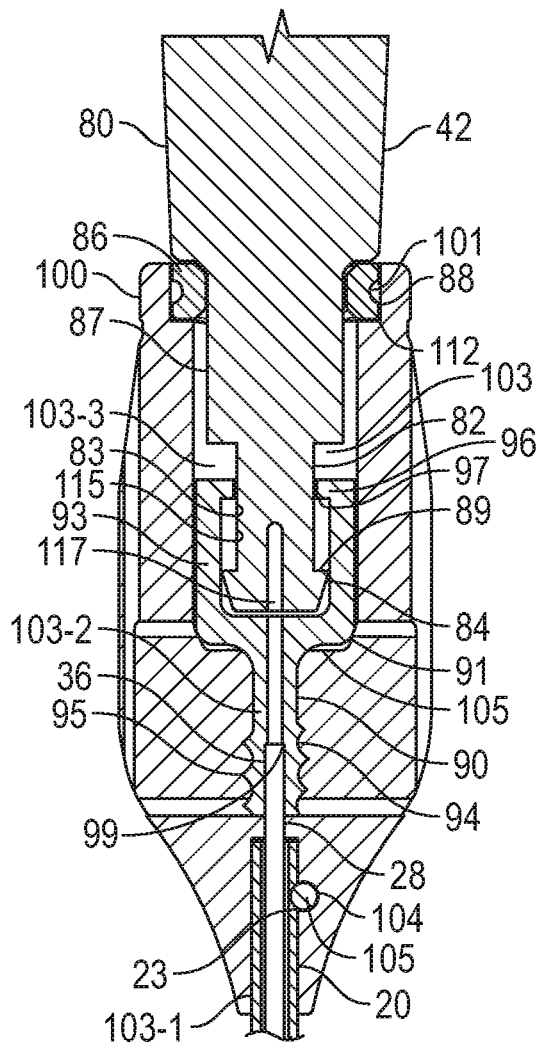
FIG. 9 illustrates the handle of the implant delivery device, according to some example embodiments.

FIG. 3 illustrates an expanded view of a portion of the implant delivery device 40 including the cannulated outer shaft 26, the inner shaft 28, the implant holder portion 44, and the connector 46. Again, while the implant holder portion 44 and the cannulated outer shaft 26 are shown as two separate components, they can be formed as one integral component. Similarly, the connector 46 is shown as a separate component from the inner shaft 28, but can be formed as one integral component. The cannulated outer shaft 26 and the inner shaft 28 extend from the handle 18 as shown in FIGS. 9 and 12A-12E. For example, the cannulated outer shaft 26 defines a bore 29 extends from a first end 35 to a second end 37. The first end 35 is non-rotationally coupled within the implant actuator 43 of the handle 18. In one example, the first end 35 can include a locking hole 23 that can receive a locking pin 105 (as shown in FIG. 9) that extends through a locking hole 104 of the implant actuator 43 and through the locking hole 23 to prevent the cannulated outer shaft 26 from rotating or moving longitudinally relative the implant actuator 43.

As seen in FIGS. 2 and 3, the implant holder portion 44 includes a connector portion 58 including a projection 59. The projection 59 is non-rotationally coupled to the cannulated outer shaft 26. For example, the projection 59 is non-rotationally coupled within the bore 29 of the cannulated outer shaft 26. Thus, the cannulated outer shaft 26 including the implant holder portion 44 is rotationally and longitudinally locked to the implant actuator 43.

Figure 4C:
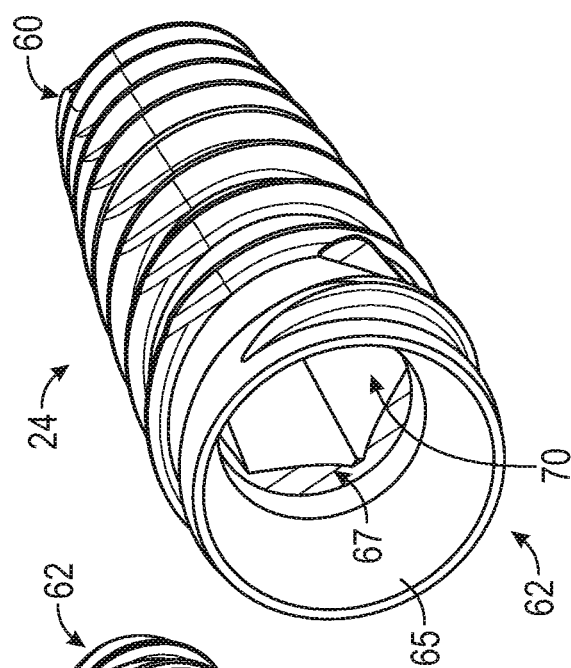
FIG. 4C illustrates a perspective view from a proximal end of the implant body in FIG. 4A, according to some example embodiments.
Figure 4B:
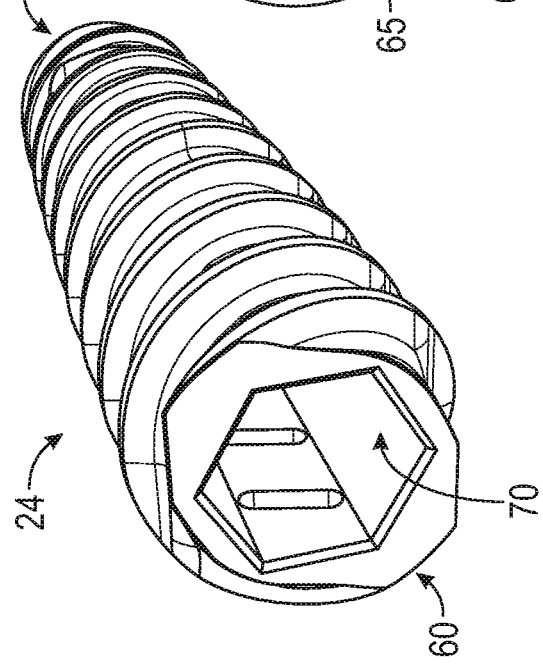
FIG. 4B illustrates a perspective view from a distal end of the implant body in FIG. 4A, according to some example embodiments.

The implant holder portion 44 includes an implant portion 56 that has a shape that matches an internal shape of a bore 70 of the implant body 24 of the implant 20 (as shown in FIGS. 4B and 4C). The implant portion 56 has a reduced diameter compared to the connector portion 58 such that a stop 45 is formed and is configured to abut a first end 60 of the implant body 24 of the implant 20 (shown in FIG. 6). When the implant body 24 is mounted onto the implant portion 56 of the implant holder portion 44 and the cannulated outer shaft 26, the implant body 24 is prevented from rotating about the implant portion 56 of the cannulated outer shaft 26. When the implant actuator 43 is rotated, the cannulated outer shaft 26 including the implant holder portion 44, and the body 24 of the anchor 20 rotate about the longitudinal axis 16 and relative to the inner shaft 28, the wire 32, and the distal member 22 of the implant 20.

The inner shaft 28 defines a bore 31 extending from a first end 39 to a second end 41. The inner shaft 28 is configured to extend through the bore 29 of the cannulated outer shaft 26. The first end 39 is non-rotationally coupled to a driver 90 positioned within the handle 18 (as shown in FIG. 9). As discussed herein, the inner shaft 28 can include the connector 46. The second end 41 includes the slots 55 and is configured to receive a portion of the connector 46. For example, the connector 46 includes a first end 47 and a second end 49. The first end 47 has a reduced diameter compared to the second end 49 and is configured to be received within the bore 31 of the inner shaft 28. When the connector 46 is coupled to the inner shaft 28, the slots 54 of the connector 46 align with the slots 55 of the inner shaft 28 to form the anchor alignment slots 57 (shown in FIGS. 2 and 6).

In the example shown, the implant 20 is a cannulated suture anchor and includes the implant body 24 and a distal member 22. The distal member 22 is coupled to the implant body 24 such that they are independently moveable with respect to each other. As discussed herein, the distal member 22 can maintain a rotational position as the implant body 24 is rotated about a longitudinal axis and inserted into the bone hole.

Figure 4A:
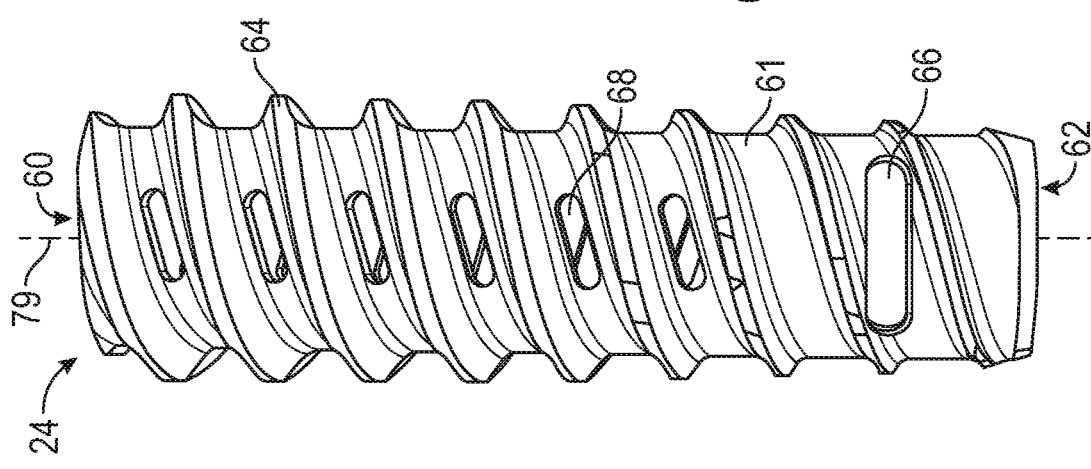
FIG. 4A illustrates a side-view of an implant body of the implant, according to some example embodiments.

As seen in FIGS. 4A-C, the implant body 24 includes at least one bone engaging feature and is configured to controllably rotate about a longitudinal axis 79 of the implant 20 (coinciding with longitudinal axis 16 of the implant delivery device in FIG. 1). The implant body 24 the bone engaging features can have an external diameter larger than a diameter of the bore in the patient. As the surgeon initiates the rotation from the handle 18, the implant body 24 can rotate about the longitudinal axis 79, and the bone engaging features can implant into the wall of the bore. Friction between the bone and the implant body 24 can secure the implant 20 in place in the bore after the surgical procedure has been completed. This friction can, in turn, secure the sutures in place, as well.

The implant body 24 can extend from a proximal end 60 to a distal end 62 and include a bore 70 extending from the proximal end 60 to the distal end 62. The implant body 24 can include bone engaging features 64 positioned on an exterior surface 61. In the example shown, the bone engaging features 64 include threads, such as helical threads. It should be appreciated, however, that various other bone engaging features 64 may be utilized, such as ribs or protrusions. The implant body 24 can include a distal member opening 66 and fenestrations 68. The bore 70 at the distal end 62 can include a tapered section 65 and an annular groove 67.

Figure 5A:
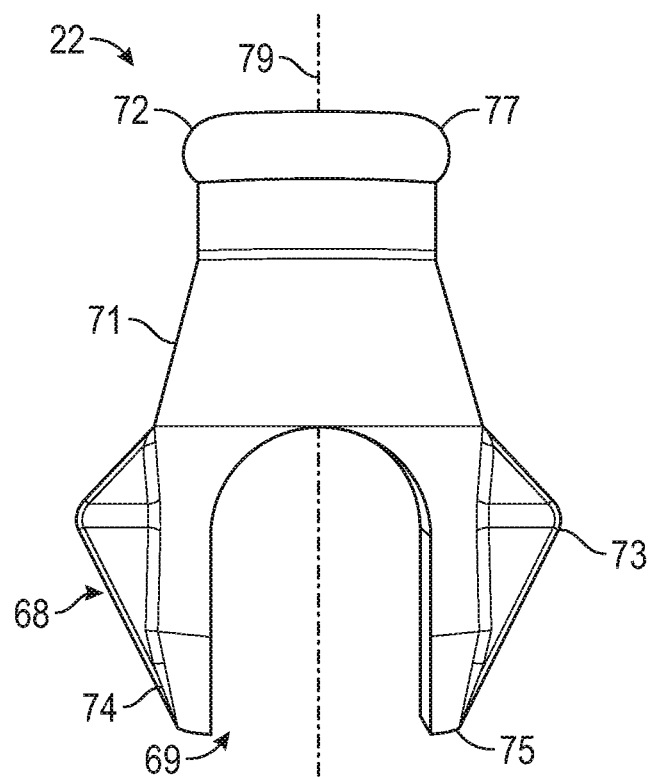
FIG. 5A illustrates a side view of a distal member of the implant, according to some example embodiments.
Figure 5B:
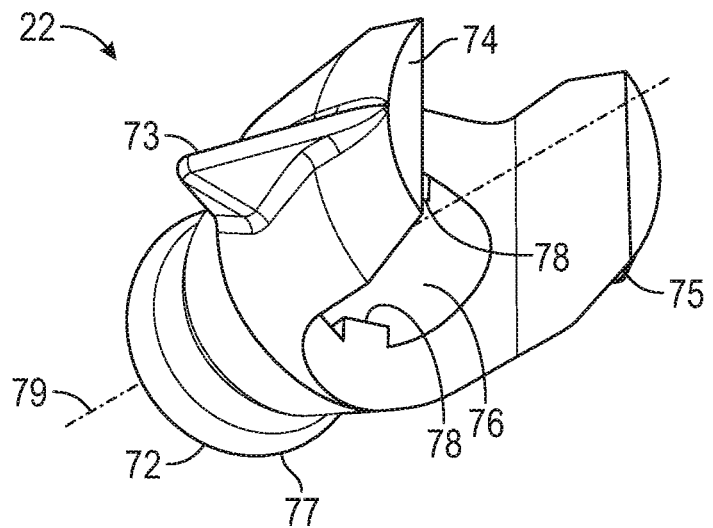
FIG. 5B illustrates a perspective view from a proximal end of the distal member in FIG. 5A.

As shown in FIGS. 5A and 5B, the distal member 22 can include a proximal end 72, a distal end 74, and a bore 76. The proximal end 72 can include an annular ring 77 and the distal end 74 can include a suture retention portion 68. In the example shown, the suture retention portion 68 includes two distally extending prongs 75 on opposite sides of the longitudinal axis 79 that define a recess 69 or depression that can receive and prevent sutures from sliding around or off of the distal member 22.

The two distally extending prongs 75 can include bone engaging features 73. In the example shown, the bone engaging features includes a projection extending in a direction perpendicular to the longitudinal axis 79. The distal member 22 can also include transitional section 71 having a tapered profile. Further, the internal surface defining the bore 76 can include projections 78 extending into the bore 76 toward the longitudinal axis 79. As discussed herein, the projections 78 are configured to be positioned within the anchor alignment slots 57 (see FIG. 6). Thus, the number of projections 78 can equal the number of anchor alignment slots 57 formed on the anchor guide 28.

Figures 6A, 6B:
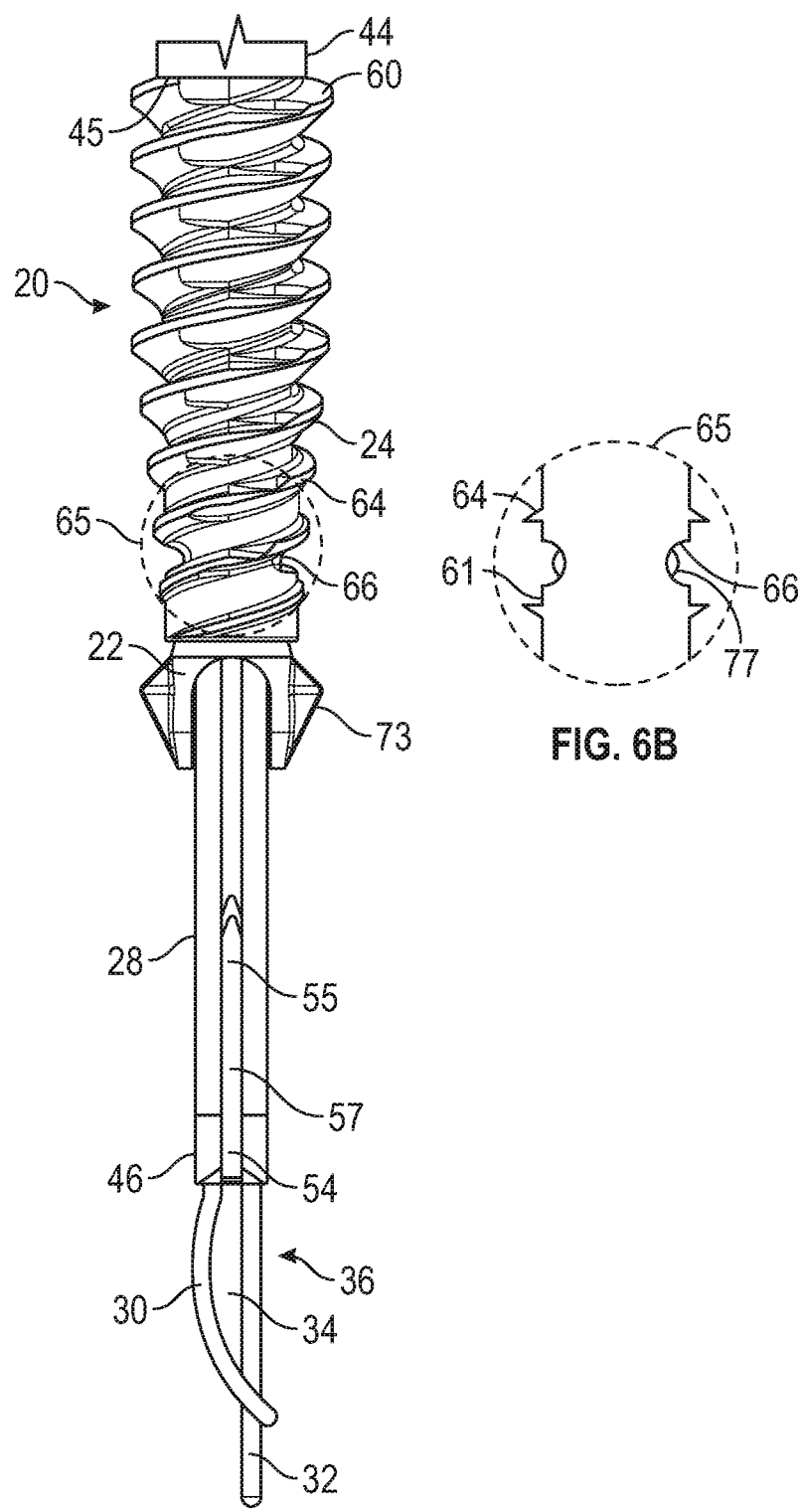
FIG. 6A illustrates a side view of the implant mounted on the implant delivery device, according to some example embodiments.
FIG. 6B illustrates a close-up of a portion of the implant in FIG. 6A, according to some example embodiments.

Referring to FIGS. 5A, 5B, 6A, and 6B, the distal member 22 can be coupled to the implant body 24. For example, the distal member 22 can be positioned within the implant body 24 of the implant 20 such that the annular ring 77 is positioned within the annular groove 67 of the implant body 24 and the transitional section 71 is positioned within the tapered section 65 of the bore 70. As seen in FIGS. 6A-B, the annular ring 77 is positioned within the distal member opening 66 but does not extend past the exterior surface 61 (see FIG. 6B). Thus, while the distal member 22 is "free floating" with respect to the implant body 24, the distal member 22 and the implant body 24 are longitudinally locked with respect to each to each other. In other words, the distal member 22 and the implant body 24 can rotate independent of each other but the longitudinal position between the distal member 22 and the implant body 24 is maintained. That is, the distal member 22, and the implant body 24 are longitudinally coupled but not rotationally coupled to each other.

When the implant 20 is mounted to the implant delivery device 40, a portion of the bore 70 of the implant body 24 is positioned around the implant portion 56 of the cannulated outer shaft 26 along the implant holder portion 44. As seen in FIGS. 3, 4B, and 4C, the implant portion 56 has an exterior surface and the bore 70 has an interior surface that have corresponding non-rotational shapes such that the implant body 24 is non-rotationally mounted to the implant holder portion 44. The distal member 22 coupled to the threaded portion 24 and is aligned such that the projections 78 are positioned within the anchor alignment slots 57.

As discussed herein, during insertion of the implant 20 into a bone hole, the distal member 22 does not rotate with the implant body 24 when a rotational force is applied to the implant body 24, via a user rotating implant actuator 43. As the rotational force is applied to the implant body 24, the implant 20 moves distally. As the implant body 24 rotates, the distal member 22 does not rotate and maintains a substantially constant radial position as the projections 78 move within the anchor alignment slots 57 and the anchor 20 moves distally. Since the distal member 22 is "free floating" with respect to the implant body 24, the distal member 22 does not rotate as the body 24 rotates to engage the bone of the bone hole.

The implant 20 can be formed of any appropriate biocompatible material including polymers, co-polymers, such as polyetheretherketone (PEEK), metals, such as titanium, and various alloys, formed from titanium, cobalt, chromium, etc.

Figure 7:
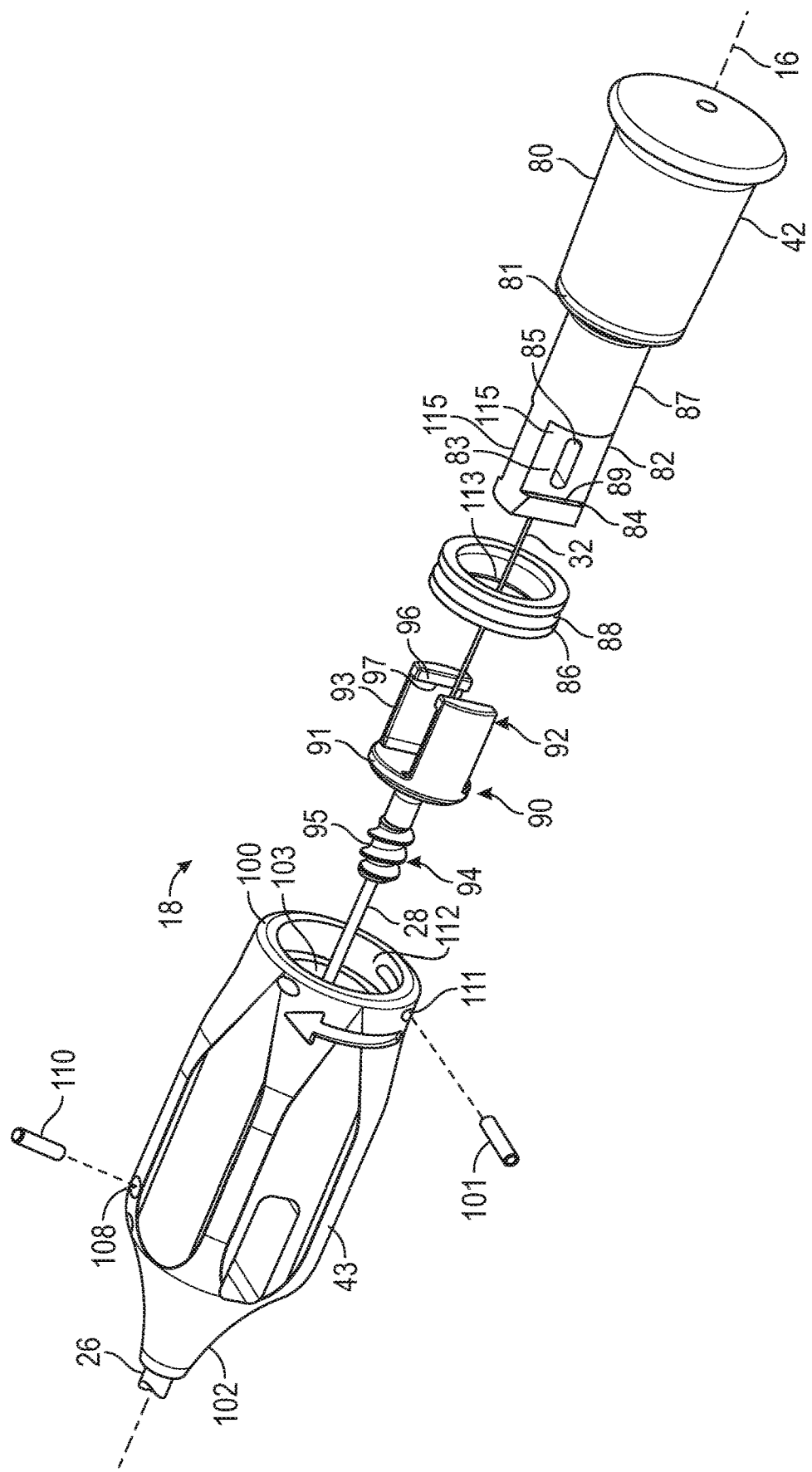
FIG. 7 illustrates an expanded view of the implant delivery device, according to some example embodiments.
Figure 8:
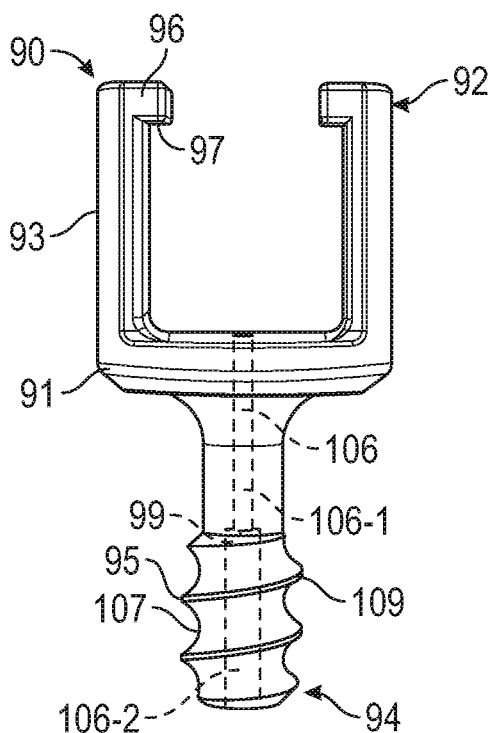
FIG. 8 illustrates a driver of the handle of the implant delivery device, according to some example embodiments.

FIG. 7 illustrates an expanded view of the handle 18, the cannulated outer shaft 26, the inner shaft 28, and the wire 32. The handle 18 includes the wire actuator 42 (also referred to herein as "proximal handle portion"), the implant actuator 43 (also referred to herein as "distal handle portion"), a washer 86, a driver 90, and driver pins 110. As discussed herein, the wire actuator 42 is used to move the wire 32 distally and proximally such that eyelet 34 (as shown in FIG. 6A) defined by the wire 32, the projection 30, and distal end 27 of the inner shaft 28 can transition between an open and closed loop. The implant actuator 43 can be used to apply a rotational force to the implant body 24 of the implant 20 to insert the implant 20 into a bone hole. The wire 32 is coupled to the wire actuator 42 such that the movement of the wire actuator 42 relative to the implant actuator 43 causes the eyelet 34 (see FIG. 6A) to transition between the open and closed configurations.

Figure 10:
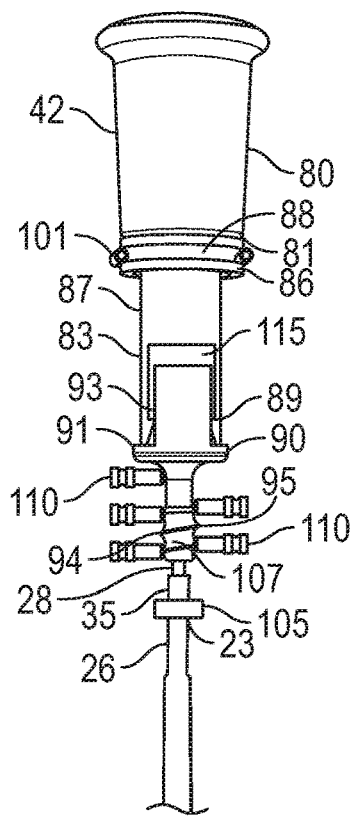
FIG. 10 illustrates a portion of implant delivery device including a wire actuator of the handle, according to some example embodiments.

Referring to FIGS. 7, 9, and 10, the wire actuator 42 can include a first end 80 and a second end 82. The first end 80 is configured to be positioned outside of the implant actuator 43 and defines a stop 81 that is configured to contact a proximal end 100 of the implant actuator 43. The second end 82 of the proximal handle 42 is configured to move within the implant actuator 43. For example, the second end 82 includes a first portion 87 and a second portion 83. The first portion 87 has a reduced diameter compared to the first end 80. As seen in FIG. 9, the washer 86 is positioned at the proximal end 100 of the distal handle 43. In one example, the proximal end 100 of the distal handle 43 defines an annular recess 112 and a projection 101. The washer 86 includes a groove 88 such that the when the washer is positioned within the annular recess 112 the projection 101 is positioned within the groove 88. In an example, the projection 101 is a pin that is inserted through a hole 111 in the implant actuator 43.

The washer 86 further defines an opening 113 configured to receive the first portion 87. The diameter of the opening 113 can be complimentary to an external diameter of the first portion 87 such that the first portion 87 can be slidably moved through the opening 113. In one example, the diameter of the opening 113 can be sized and shaped to provide a relatively tight or snug fit so as to prevent any unintended movement of wire actuator 42 relative to the implant actuator 43.

The second portion 83 includes at least one a non-rotational surface 115 and a projection 84 defining a shoulder 84. In the example shown, the second portion 83 includes two non-rotational surfaces 115. As seen in FIG. 9, the second portion 83 is positioned within a portion of the driver 90. In the example shown, the non-rotational surface 115 is a recessed flat surface. The non-rotational surface 115 positioned within the driver 90 allows the wire actuator 42 and the driver 90 to be rotationally locked together. That is, the wire actuator 42 cannot rotate relative to the driver 90. As discussed herein, as the implant actuator 43 is rotated about the longitudinal axis 16 while holding the wire actuator 42 stationary, the implant actuator 43 moves distally along the driver 90 and relative to the wire actuator 42.

The wire actuator 42 can include a bore 117 extending from the distal end of the wire actuator 42 to at least a window 85 that extends through the non-rotational surface 115. The wire 32 can extend through the bore 117, out the window 85, and wrap around the exterior surface of the second portion 83 of the wire actuator 42 to couple the wire 32 to the suture anchor 42.

Referring to FIGS. 7-10, the driver 90 includes a base 91, a first end 92 extending proximally from the base 91, a second end 94 extending distally from the base 91, and a bore 106 extending from the base 91 to the second end 94. The first end 92 includes two elongated legs 93 having a projection 96 defining a shoulder 97 extending from a proximal end of the two elongated legs 93. The second end 94 includes a threaded driver 95 having a thread defining a crest 109 and a groove 107. As discussed herein, the driver pins 110 extend through a body of the implant actuator 43 and can cooperate with the threaded driver 95 such that as the implant actuator 43 is rotated, the driver pins 110 move along the groove 107 of the threaded driver 95, thereby moving the implant actuator 43 relative to the wire actuator 42. The bore 106 of the driver 90 includes a first portion 106-1 and a second portion 106-2. The first portion 106-1 has a smaller diameter than the second portion 106-2 and a stop 99 is defined between the first portion 106-1 and the second portion 1062. The wire 32 passes through the driver 90 via bore 106 and into the wire actuator 42. The second portion 106-2 of the bore 106 is configured to receive and non-rotationally couple to the inner shaft 28. For example, the first end 36 of the inner shaft 28 can have a non-rotational shape that can match a shape of the second portion 106-2 of the bore 106. The inner shaft 28 is inserted into the bore 106 until the firs tend 36 of the inner shaft 28 contacts the stop 99.

The implant actuator 43 includes a proximal end 100, a distal end 102, and a bore 103 extending from the proximal end 100 to the distal end 102. As discussed herein, the proximal end 100 includes the annular recess 112 configured to receive the washer 86. The bore 103 includes a first portion 103-1, a second portion 103-2, and a third portion 103-3. The first portion 103-1 located at the distal end 102 is configured to non-rotationally couple with the cannulated outer shaft 26. The first portion 103-1 and the distal end 35 of the cannulated outer shaft 26 can have corresponding shapes that prevent rotation. Further, the implant actuator 44 can include a locking hole 104 configured to receive a locking pin 104 that can pass through the locking hole 23 on the cannulated outer shaft 26 to longitudinally couple the cannulated outer shaft 26 within the implant actuator 43.

Figure 11:
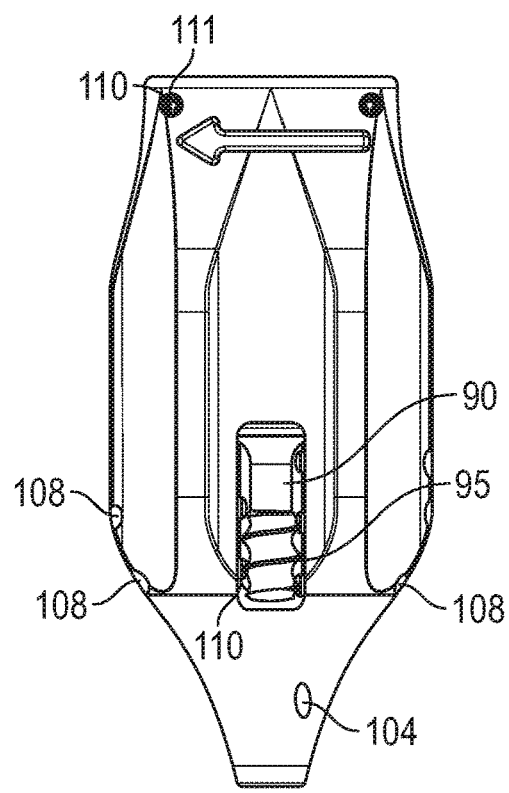
FIG. 11 illustrates a portion of implant delivery device including an implant actuator of the handle, according to some example embodiments.

The second portion 103-2 of the bore 103 is configured to receive the threaded driver 95. The implant actuator 43 includes driver holes 108 (see FIGS. 7 and 11) extending from an external surface to the second portion 103-2 of the bore 103. Driver pins 110 can extend through the driver holes 108 and engage with the threaded driver 94 of the driver 90.

The position of the implant actuator 43 relative to the driver 90 can change by rotating the distal handle 43 while the proximal handle 42 is held stationary. The implant actuator 43, cannulated outer shaft 26, and the implant body 24 of the implant 20 are all non-rotationally coupled to each other. That is, the rotation of the implant actuator 43 will also rotate the cannulated outer shaft 26 and the implant body 24 of the implant 20. Similarly, the wire actuator 42, the driver 90, the inner shaft 28, and the wire 32 are non-rotationally coupled to each other. Moreover, while non-rotationally coupled, the wire actuator 42 can move longitudinally with respect to the driver 90, the cannulated outer shaft 26, the inner shaft 28, and the implant 20. For example, the implant actuator 43 can be held stationary and the wire actuator 42 can move relative to the implant actuator 43 thereby moving the wire 32 distally or proximally relative to the driver 90, the cannulated outer shaft 26, the inner shaft 28, and the implant 20. The movement of the wire actuator 42 is limited by the length of the two elongated legs 93. For example, the wire actuator 42 can move proximally until the shoulder 84 of the wire actuator 42 contacts the shoulder 97 of the driver 90. Further, the wire actuator 42 can move distally until the distal end of the wire actuator 42 contacts the base 91 of the driver 90.

Figure 13:
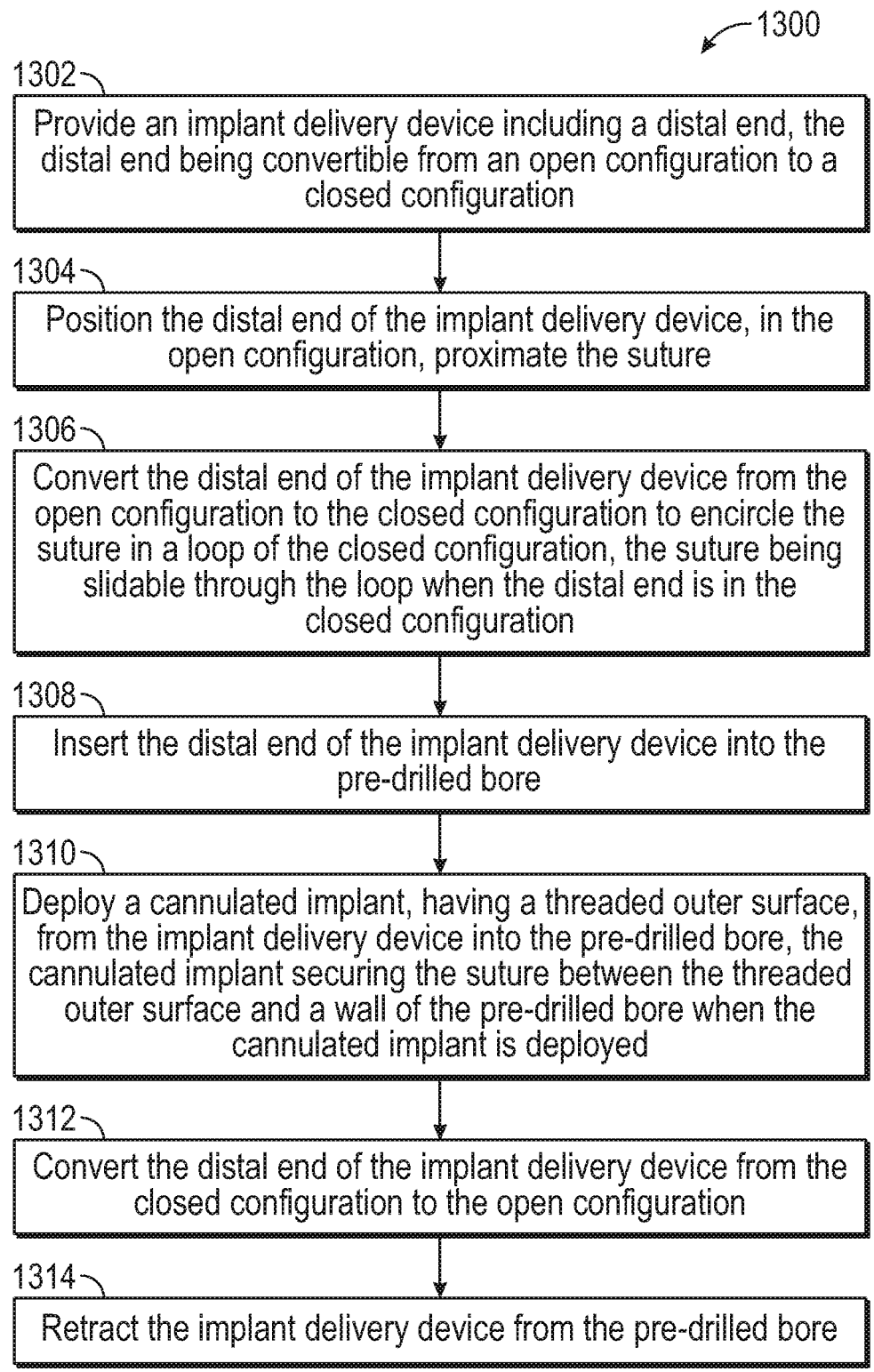
FIG. 13 shows a flow chart of an example of a method for securing a suture to a pre-drilled bore, according to some example embodiments.

FIGS. 12A-12F illustrate a method of deploying an anchoring device such as implant 20 for anchoring a sutured tissue to a bone with an implant delivery device 40. As discussed herein, the handle 18 can include a wire actuator 42 at a proximal end of the handle 18, and an implant rotator 43 distal to the wire actuator 42. By translating the wire actuator 42 proximally or distally with respect to the implant rotator 43, a surgeon can proximally retract or distally advance the wire 32 with respect to the inner shaft 26 (FIGS. 12A-B). By rotating the implant rotator 43 with respect to the wire actuator 12, the surgeon can rotate the implant body 24 around the longitudinal axis 16 (see FIG. 1). FIG. 13 shows a flow chart of an example of a method 1300 for securing a suture to a pre-drilled bore, according to some example embodiments. As discussed herein, the method 1300 shown can be accomplished with the implant delivery device shown in FIGS. 1-12 and with the implant delivery device in FIGS. 14-22.

In an example, method 1300 includes providing an implant delivery device including a distal end, the distal end being convertible form an open configuration to a closed configuration 1302, positioning the distal end of the implant delivery device, in the open configuration, proximate the suture 1304, converting the distal end of the implant delivery device form the open configuration to the closed configuration to encircle the suture in a loop of the closed configuration, the suture being slidable through the loop when the distal end is in the closed configuration 1306, inserting the distal end of the implant delivery device into the pre-drilled bore 1308, deploying a cannulated implant, having a threaded outer surface, from the implant delivery device into the pre-drilled bore, the cannulated implant securing the suture between the threaded outer surface and a wall of the pre-drilled bore when the cannulated implant is deployed 1310, converting the distal end of the implant delivery device form the closed configuration to the open configuration 1312, and retracting the implant delivery device from the pre-drilled bore.

In FIG. 12A, the implant delivery device 40 has a distal end that can be convertible form an open configuration to a closed configuration. To covert the distal end from a closed configuration to the open configuration, the wire actuator 42 has been pulled proximally from the implant rotator 43, so that the wire 32 is proximally retracted in the inner shaft 26 and the closed loop is open. The sutures 120 can be placed proximate to the projection 30, e.g., onto the projection 30. At this stage of the surgery, the surgeon has positioned the implant delivery device 40 so that the sutures 116 extend along a distal end of the inner shaft 28 or the projection 30, and the wire 32 is retracted proximally. Next, the surgeon manipulates the wire actuator 42 distally toward the implant rotator 43 to distally advance the wire 32 to contact the projection 30, thereby closing the loop. The sutures 120 pass through the closed loop, i.e., eyelet 34 (see FIG. 6), so that the surgeon can position the sutures 120 by positioning the implant delivery device 40.

After the loop is closed, the surgeon can insert a distal end of the implant delivery device 40, with the sutures 120, into the bore 122 in the bone. In FIG. 12B, the surgeon has closed the loop by moving the actuator 42 distally relative to the implant actuator 43 and has advanced the implant delivery device 40 distally until the sutures 120 are at or near a bottom of the bore 122. With the implant delivery device 40 positioned as in FIG. 12B, the sutures 120 extend into the bore 122 through the eyelet 34 and out of the bore 122. At this point, the surgeon can adjust the sutures 120 at locations away from the implant delivery device 40, if needed. For example, if needed, the surgeon can tighten the sutures 120 at respective tissue sites, such as for a rotator cuff under repair Next, the surgeon can manipulate the implant actuator 43 relative to the wire actuator 42 to rotate the implant body 24 about the longitudinal axis. For example, while holding the wire actuator 42 in a constant radial position, the surgeon can rotate the implant actuator 43, which will translate the rotational motion to the implant body 24, as discussed herein. Such manipulation can distally advance the implant 20 into the bore 122, as the threads on the implant body 20 engage the wall of the bore 122. As the implant body 24 rotates, the distal member 22 of the implant 20 maintains a constant rotational position, while moving distally. That is, as the implant body 24 rotates and engages with bone, the same distal member 22 does not rotate but moves distally as the implant body 24 is advanced. The sutures 120 extend distally along one side of the implant body 20 between the threads and the wall of the bore 122, pass through the loop, e.g., eyelet 34 (formed by the wire 32, the projection 30, and the distal end of the inner shaft 28), and extend proximally along an opposite side of the implant body 24 between the threads and the wall of the bore 122. During this advancement of the implant 20, the inner shaft 28, projection 30, and wire 32 can remain at the same longitudinal position along the bore 122. In FIG. 12C, the surgeon is halfway through the advancing the implant 20.

The surgeon can distally advance the implant 20 into the bore 122 at least until a proximal end of the implant 20 is flush with a surface 124 of the bone. In FIG. 12D, the surgeon has fully advanced the implant 20 into the bore 122. At this position, the distal member 22 can be positioned next to the sutures 120, so that the distally-extending prongs on the distal member 22 extend on opposite sides of the sutures 120.

Next, the surgeon can manipulate the wire actuator 42 proximally with respect to the implant actuator 43 to withdraw the wire 32 into the inner shaft 28, thereby opening the loop and freeing the sutures 120 from the implant delivery device 40. In FIG. 12E, the loop has been opened such that implant delivery device 40 can be withdrawn without catching on the sutures 120.

Next, the surgeon can proximally withdraw the implant delivery device 40 including the cannulated outer shaft 26, the inner shaft 26, the projection 30, and the wire 32 from the bore 122, leaving the implant 20 (including the implant body 24 and the distal member 22) and the sutures 120 in the bore 122. In FIG. 12F, just the implant body 24, the distal member 22, and the sutures 120 remain in the bore 122. The sutures 122 extend distally along one side of the implant body 24 between the threads and the wall of the bore 122, pass between the distally-extending prongs of the distal member 22, and extend proximally along an opposite side of the implant body 24 between the threads and the wall of the bore 122. The threads form an interference fit that holds the sutures 120 in place. In the stage of FIG. 12F, the implant is fully implanted.

The elements shown in FIGS. 12A-F can be positioned at a distal end of the implant delivery device 20. At a proximal end of the implant delivery device 40, a handle can control the rotation of the implant body 24 and a proximal/distal position of the wire 32. There are many possible configurations for such a handle. FIGS. 12A-E show one such configuration.

In FIGS. 1-12, the handle 18 was used to control the rotation of the implant body 24 and the proximal/distal position of the wire 32. For example, the wire actuator 42 (positioned proximally to the implant rotator 43; referred to as the proximal handle) is held at a constant radial and longitudinal position while the implant rotator 43 (positioned distally to the wire actuator 43; referred to as distal handle) is rotated about the longitudinal axis and advanced distally as the implant rotator 43 rotates about the longitudinal axis.

FIGS. 14-22 show another configuration of an implant delivery device 200 that can be used with the implant 20 described herein. The implant delivery device 200 extends from a proximal end 202 to a distal end 204. The difference between the implant delivery device 200 and the implant delivery device 40 is that implant delivery device 200 includes handle 208. Similar to the implant delivery device 40, the implant delivery device 200 includes the same elements distal to the handle 208 as the elements distal to the handle 18 in the implant delivery device 40. That is, the implant delivery device 200 includes the cannulated outer shaft 26, the inner shaft 28, the wire 32, the projection 30, the connector 46, and the implant holder 44. Handle 208 is different from handle 18 in that the wire actuator 205 is located distal to the implant actuator 206 compared to the wire actuator 42 of handle 18 that is located proximal to implant actuator 43.

As discussed herein, as the implant actuator 206 is held stationary and the wire actuator 205 is pulled proximally, the wire actuator 205 is coupled to the wire 32 such that the wire 32 is retracted and sutures can be placed onto the projection 30. During insertion of the implant 20 into the patient, the wire actuator 205 can be held stationary and the implant actuator 206 can be rotated, which will translate the rotational motion to the implant 20.

Figure 14:
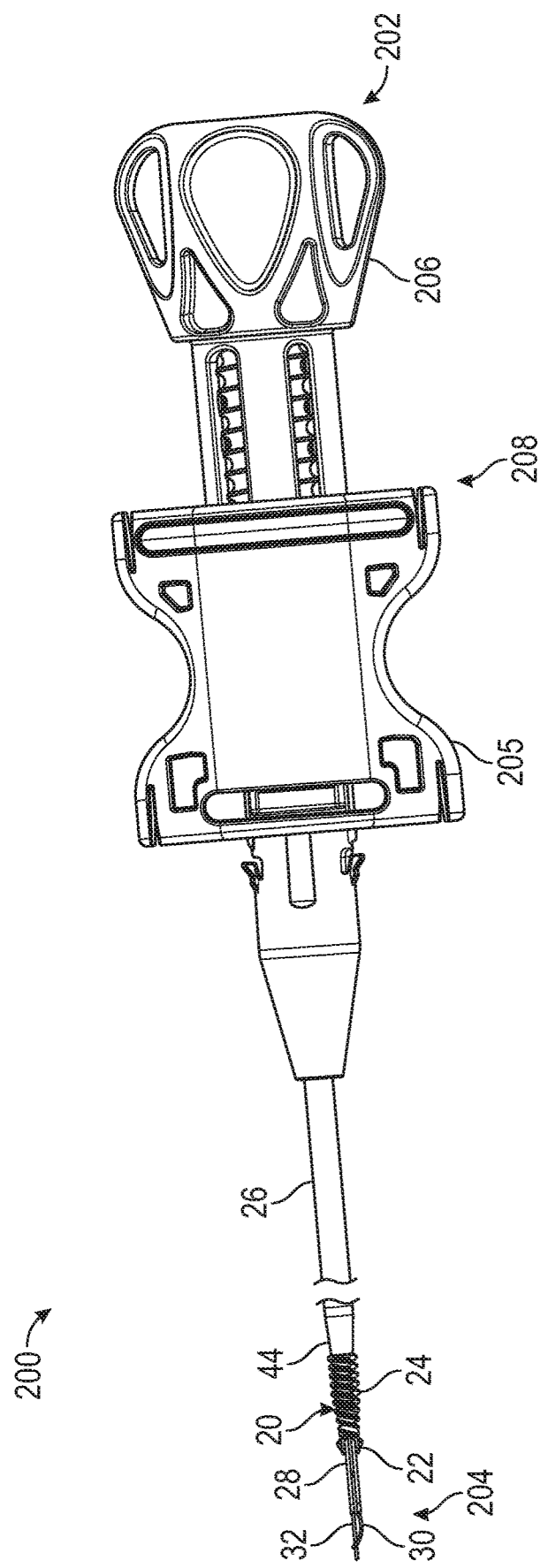
FIG. 14 illustrates a perspective view of a system for soft tissue repair including an implant delivery system and an implant, according to some example embodiments.
Figure 15:
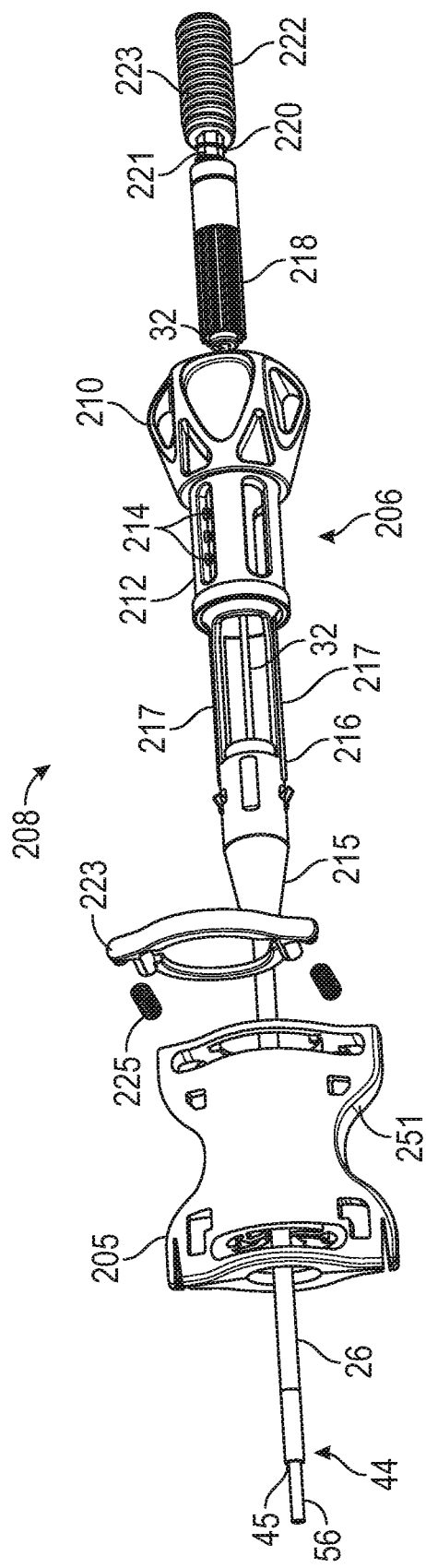
FIG. 15 illustrates an expanded view of a portion of the implant delivery system shown in FIG. 14, according to some example embodiments.

FIG. 15 illustrates an expanded view of a portion of the implant delivery 200 system shown in FIG. 14, according to some example embodiments. The implant delivery system 200 includes the implant actuator 206 and the wire actuator 205. The implant actuator 206 includes a grip 210, a driving portion 212, and a ratchet portion 216.

Figure 16:
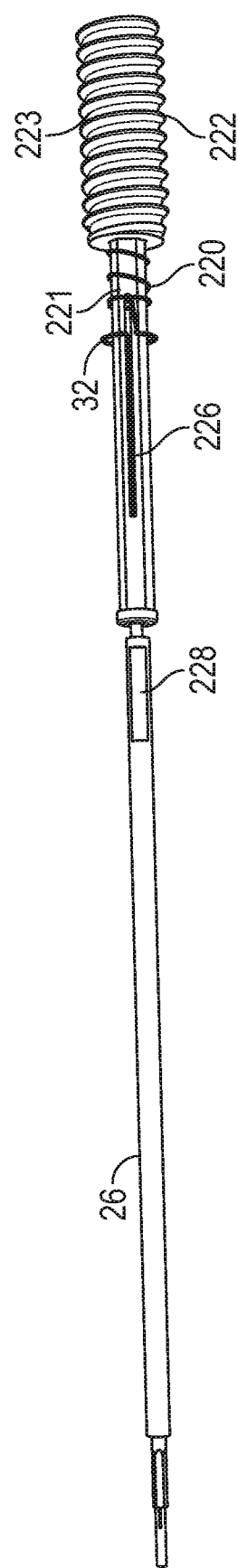
FIG. 16 illustrates a perspective view of a portion of the implant delivery system shown in FIG. 14, according to some example embodiments.
Figure 17:
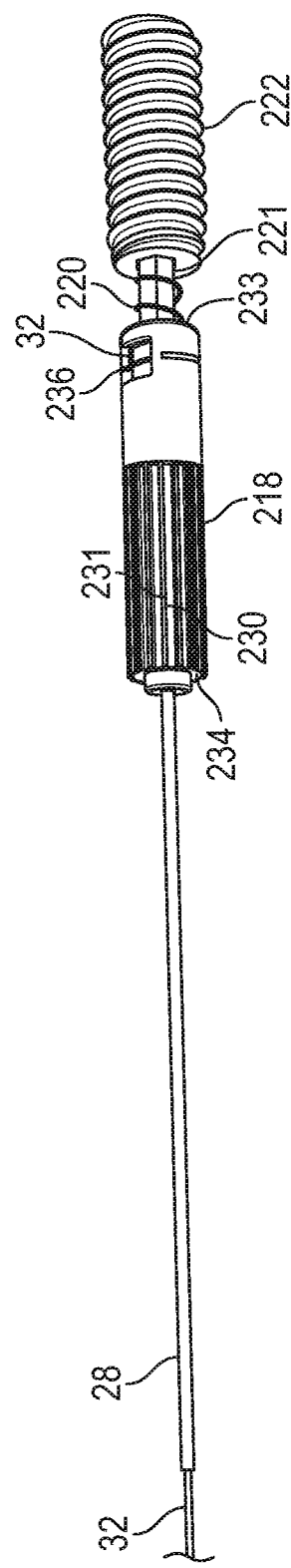
FIG. 17 illustrates a perspective view of a portion of the implant delivery system shown in FIG. 14, according to some example embodiments.

The wire 32 can extend into an internal connector 221. The internal connector 221 can be non-rotationally coupled to a threaded driver 222 and an actuating ratchet 218. As seen in FIGS. 16 and 17, the internal connector 221 can include a non-rotational cross-sectional shape that can match an internal bore shape of the threaded driver 222 and the actuating ratchet 218. In an example, the wire 32 extends through the inner shaft 28, through the internal connector 221, out a slot 226 of the internal connector 221 and through a slot 236 of the actuating ratchet 218 and wound around a portion of the actuating ratchet 218. The wire 32 is thus coupled to the actuating ratchet 218. The slot 236 in the internal connector 221 has dimensions such that the actuating ratchet 218 and wire 32 can move longitudinally relative to the internal connector 221.

The actuating ratchet 218 extends from a proximal end 233 to a distal end 234. A plurality of grooves 230 with a plurality of ridges 231 between adjacent groves 230 are provided and extend from the distal end 234 toward the proximal end 233. The internal connector 221, threaded driver 222, and the actuating ratchet 218 can be positioned within the implant actuator 206 such that the actuating ratchet 218 is positioned within the ratchet portion 216 and the threaded driver 222 is positioned within the driving portion 212.

Figure 18:
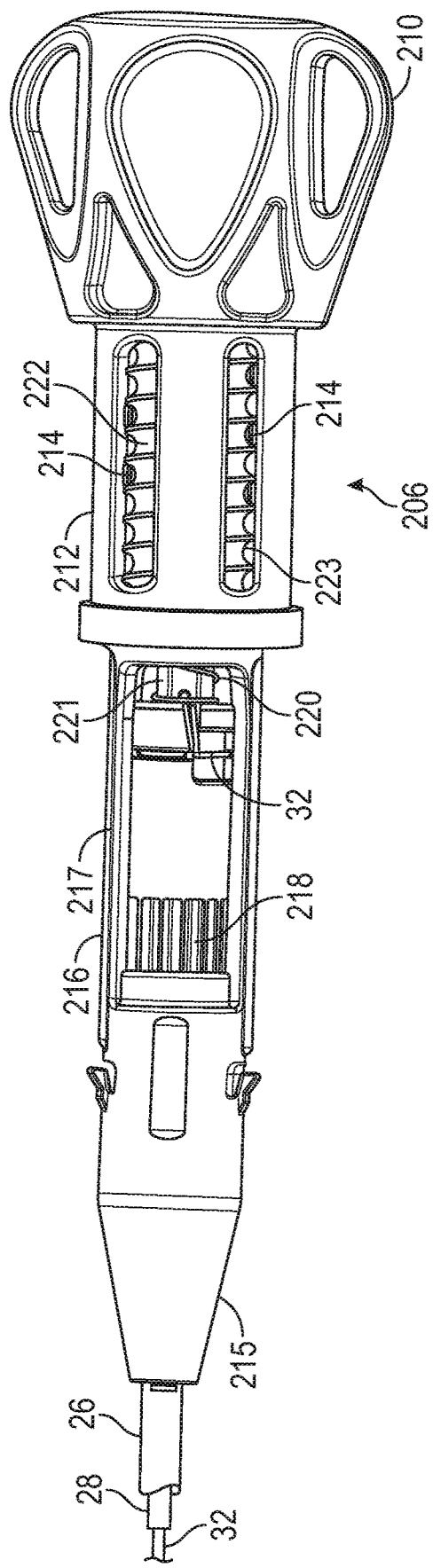
FIG. 18 illustrates a side view of a portion of the implant delivery system shown in FIG. 14, according to some example embodiments.

As seen in FIGS. 15 and 18, the driving portion 212 includes projections 214 that engage with the threads 223 on the threaded driver 222 such that when the grip 210 is rotated, the implant actuator 206 will move distally relative to the internal connector 221, threaded driver 222, actuating ratchet 218, the proximal handle 205, the wire 32, and the inner shaft 28. The rotational motion will be translated to the outer shaft 26 and rotate the implant 20 as discussed herein.

The ratchet portion 216 extends from the driving portion 212. In one example, the ratchet portion 216 includes two elongated portions 217 extending from the driving portions 212 to a tip portion 215. While shown with two elongated portions 217, one elongated portion 217 or more than two elongated portions 217 can be used.

Figure 19A:
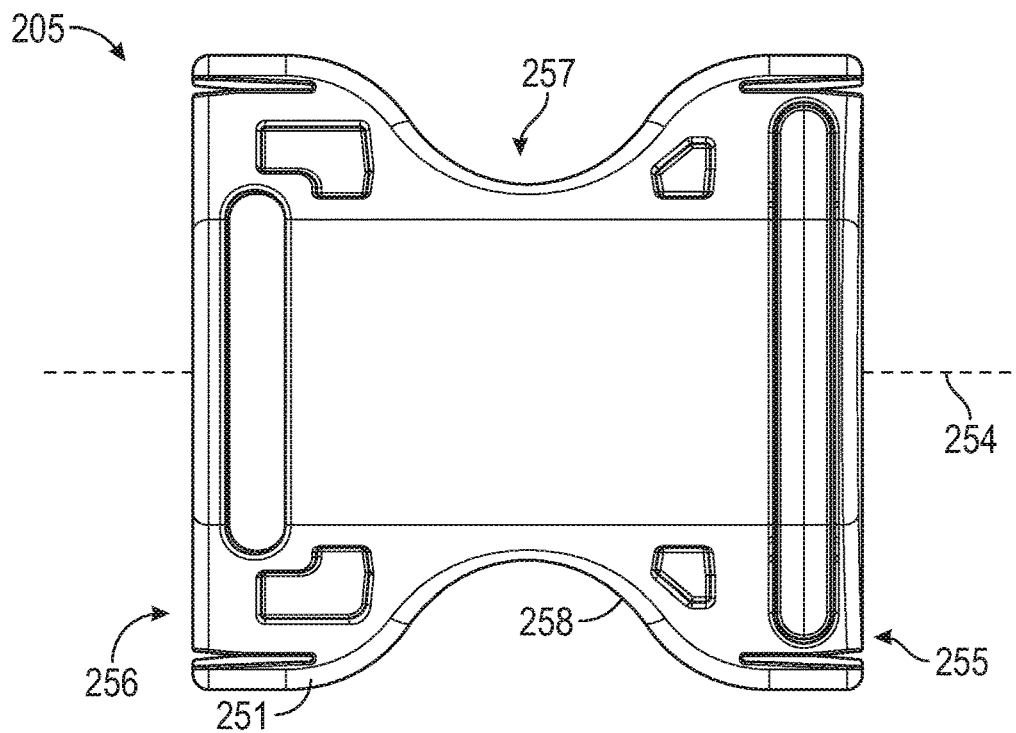
FIG. 19A illustrates a side view of the wire actuator shown in FIG. 14, according to some example embodiments.
Figure 19B:
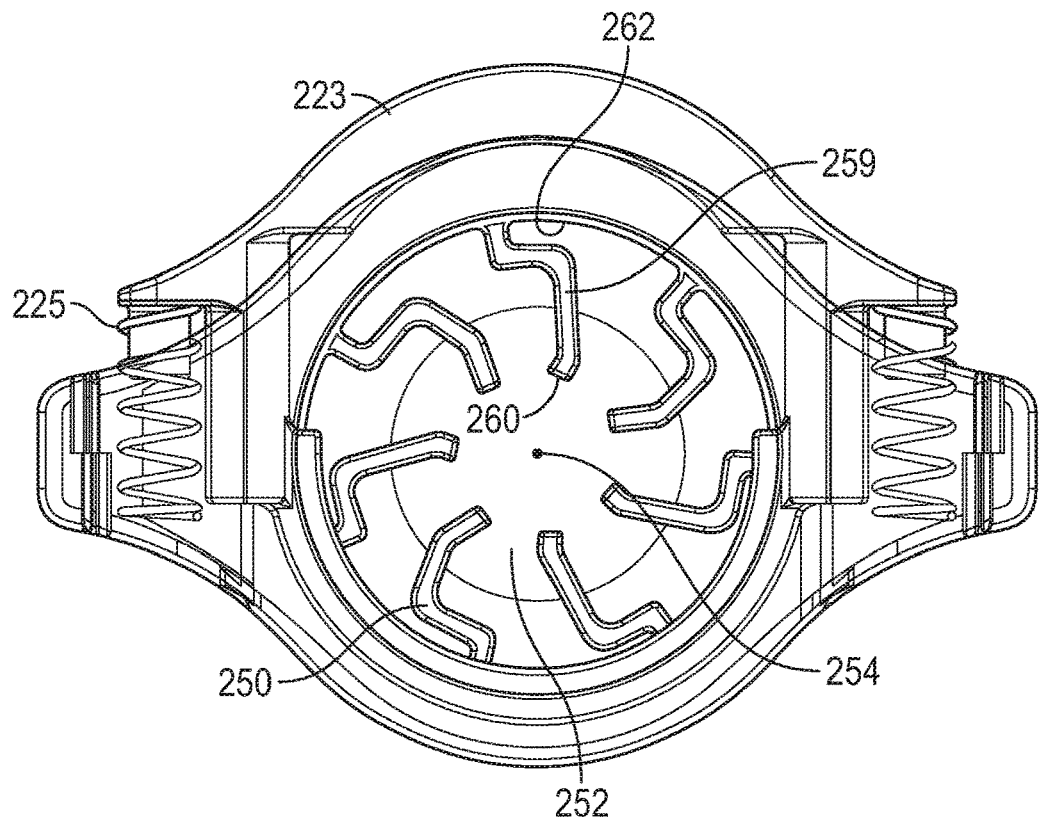
FIG. 19B illustrates a view of the wire actuator shown in FIG. 19A from the proximal end.

The wire actuator 205 is shown in FIGS. 19A & B. The wire actuator 205 includes a handle 251, a bore 252 extending through the handle 251, and a plurality of flexible arms 250 projecting inward from an inner surface 262 toward a longitudinal axis 254 of the handle 205. The handle 251 extends from a proximal end 255 to a distal end 256. The profile of the handle 251 can include a recess 257 such that a shoulder 258 is defined to assist the user in pulling the handle 251 in the proximal direction when retracting the wire 32. The wire actuator 205 also includes a release button 223 and springs 225 that can be used to remove the implant 20, if needed, as discussed herein. FIG. 19B is a view of the wire actuator 205 from the proximal end 255. As seen in FIG. 19B, the plurality of flexible arms 250 extend toward the longitudinal axis 254 from the inner wall 262. The shape and/or material of the plurality of flexible arms 250 allow the flexible arms 250 to be flexible. The plurality of flexible arms 250 include a proximal side 259 and a tip 260 that are configured to engage with the actuating ratchet 218, as discussed herein. As discussed herein, the flexibility of the flexible arms 250 allow the flexible arms 250 to bend when moving over the elongated portion 217 of the ratchet portion 216. In some examples, the flexible arms 250 can have a flexible joint where the flexible arm 250 can bend. Other configurations of the flexible arms 250 are contemplated and be based on a variety of factors.

In some instances, after advancing the implant 20 into a patient a certain amount, a surgeon may want to remove or reverse the implant 20. As discussed more herein, the release button 223 and springs 225 located, within the handle 251, can be used to disengage the flexible arms 250 from the actuating ratchet 218 such that a user can rotate the grip 210 in reverse to remove the at least partially inserted implant 20.

Figure 20:
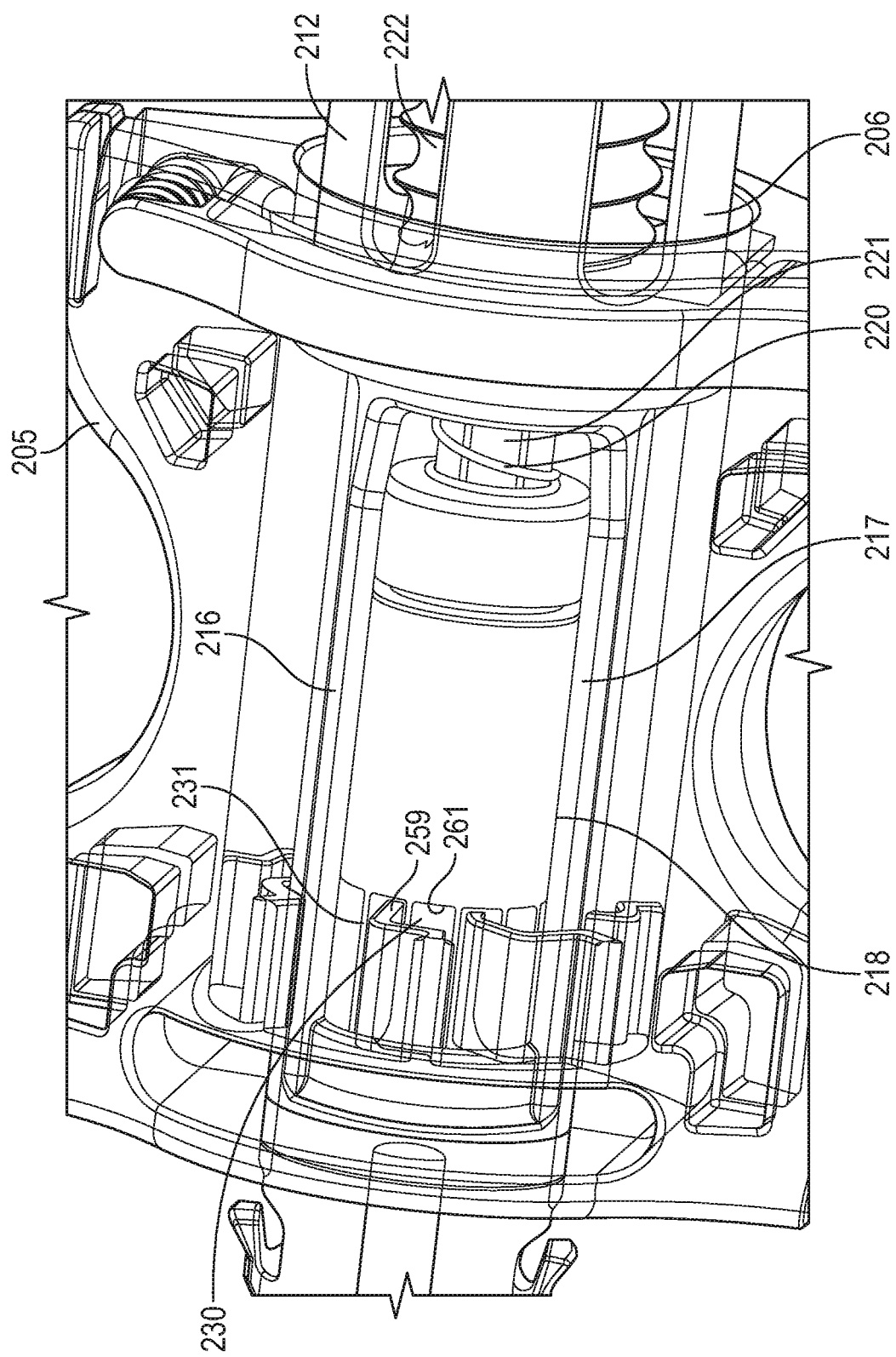
FIG. 20 illustrates a perspective view of a portion of the implant delivery device including the wire actuator positioned on an implant actuator shown in FIG. 14, according to some example embodiments.

FIG. 20 illustrates the wire actuator 205 mounted on the implant actuator 206 where at least the tip 260 of the plurality of flexible arms 250 can be positioned within a respective groove 230 of the actuating ratchet 218. As a user pulls the wire actuator 205 proximally with respect to the implant actuator 206, the proximal side 259 of the plurality of flexible arms 250 engages a proximal end 261 of the grooves 230 of the actuating ratchet 218. The proximal movement applied to the wire actuator 205 is transferred to the actuating ratchet 218 and moves the actuating ratchet 218 and the wire 32 (which is coupled to the actuating ratchet 218) proximally, thereby moving the suture grasper from a closed configuration to an open configuration. As the user moves the wire actuator 205 proximally, the spring 220 positioned around the internal connector 221 compresses. Once a user releases the wire actuator 205, the spring 220 transitions (e.g., expands) from the compressed position to a less compressed position or an uncompressed position and moves actuating ratchet 218 distally, which also moves the wire actuator 205 distally thereby closing the suture grasper automatically.

Figure 21:
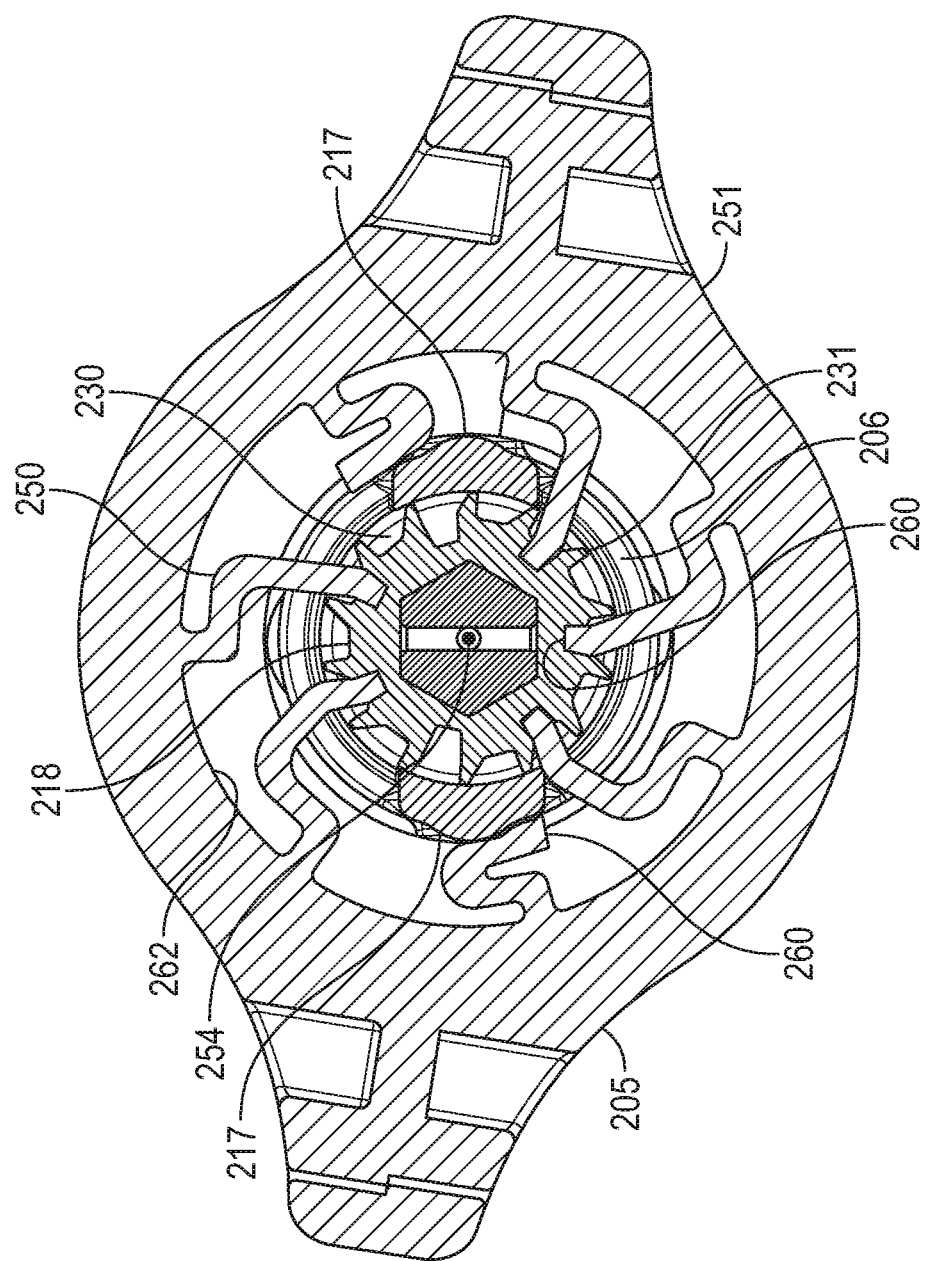
FIG. 21 illustrates a cross-sectional view along the wire actuator of the implant delivery system shown in FIG. 20.

FIG. 21 illustrates a cross-sectional view along the wire actuator 205 shown in FIG. 20. As seen in FIG. 21, the plurality of flexible arms 250 engage the grooves 230 on the actuating ratchet 218. For example, the tip 260 of the plurality of flexible arms 250 can extend into a respective groove 230. In the example shown in FIG. 21, the wire actuator 205 includes seven flexible arms 250 extending from the inner wall 262. In one example, the spacing of the flexible arms 250 and the spacing of the grooves 230 of the actuating ratchet 218 are such that allow for four of the flexible arms 250 to be engaged with, e.g., positioned within, a groove 230 of the actuating ratchet 218. The flexibility of the plurality of flexible arms 250 allow for rotation of the implant actuator 206, which extends through the bore 252 of the implant actuator 205. For example, the implant actuator 206 can include two elongated portions 217 along the ratchet portion 216. As the implant actuator 206 is rotated within the wire actuator 205, the plurality of flexible arms 250 can bend to allow the elongated portions 217 to pass. As seen in the example in FIG. 21, two of the plurality of flexible arms 250 can bend to allow the elongated portions 217 to pass while still maintaining engagement with the actuating ratchet 218 with the other flexible arms 250. The number of elongated portions 217, flexible arms 250, and grooves 230 in the actuating ratchet 218 can be based on a variety of factors. While seven flexible arms 250 and two elongated portions 217 are shown, any number of flexible arms 250 and elongated portions 217 can be utilized such that the elongated portions 217 can rotate within the handle 251 while still maintaining a secure engagement with the actuating ratchet 218.

Figure 22:
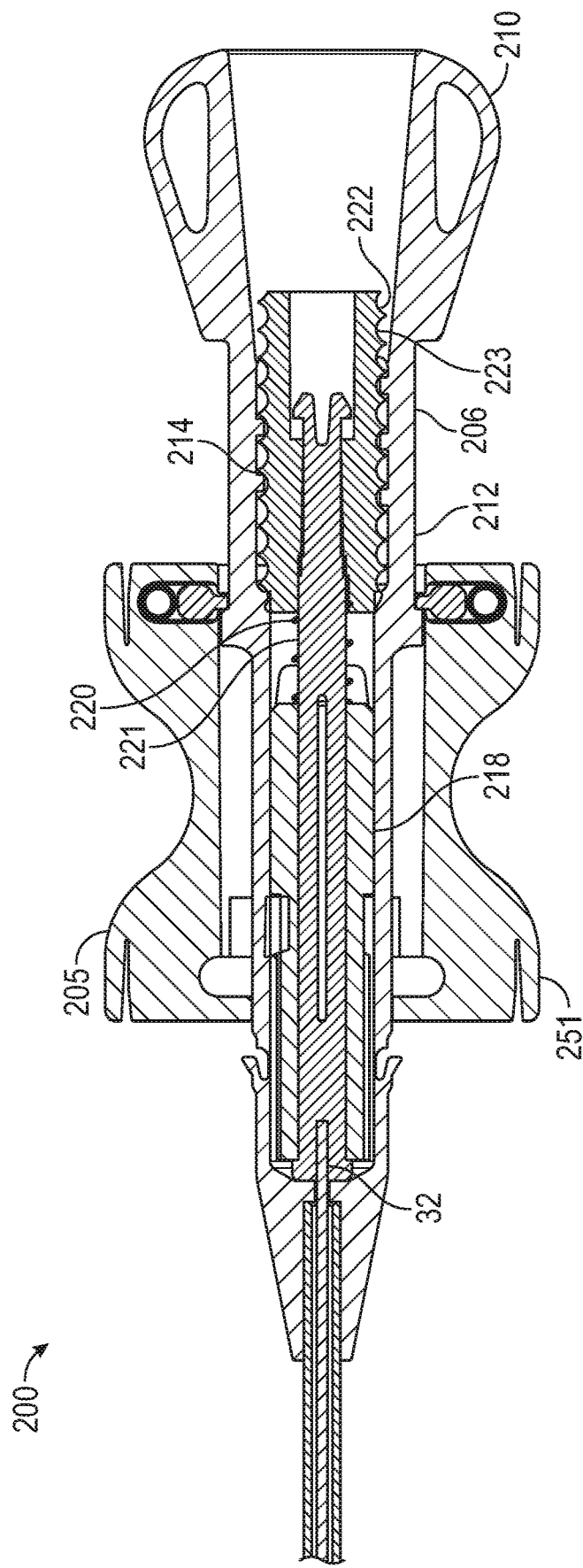
FIG. 22 illustrates a cross-sectional view along a longitudinal axis of the implant delivery system shown in FIG. 14.

FIG. 22 illustrates a cross-sectional view of the implant delivery device 200 that can be used to perform method 1300. In FIG. 22, the implant delivery device 200 has a distal end that can be convertible from an open configuration to a closed configuration, as discussed herein with respect to implant delivery device 10. To covert the distal end from a closed configuration to the open configuration, the wire actuator 205 (which is located distally with respect to the grip 210 of the implant actuator 206) can be pulled proximally toward the grip 210. As discussed herein, the wire actuator 205 is engaged with the actuating ratchet 218, which is coupled to the wire 32. As the wire actuator 205 is pulled proximally, the wire 32, the actuating ratchet 218, and the wire actuator 205 move proximally relative to the implant actuator 206, the threaded driver 222, and the internal connector 221, while compressing the spring 220.

The wire 32 is proximally retracted into the inner shaft 26 as the wire actuator 205 is moved proximally and the closed loop opens. As discussed herein, the sutures can be placed proximate to the projection, e.g., onto the projection. One the sutures are placed along the projection, the user can release or move the wire actuator distally to distally advance the wire to contact the projection, thereby closing the loop. As discussed herein, a user can release the wire actuator 205 and the spring 220 can expand to move the wire actuator 205 distally. After the loop is closed, the surgeon can insert a distal end of the implant delivery device 200, with the sutures, into a predrilled bore the bone.

Next, the user can manipulate the implant actuator 206 relative to the wire actuator 205 to rotate the implant body about the longitudinal axis. For example, while holding the wire actuator 205 in a constant radial and longitudinal position, a user can rotate the implant actuator 206 by rotating the grip 210, which will translate the rotational motion to the implant body. For example, the implant actuator 206 is non-rotationally coupled to the outer cannulated shaft, which is non-rotationally coupled to the implant body. Thus, as the drip 210 is rotated, the implant body is rotated, and the implant can distally advance into the bore. As discussed herein, as the implant body rotates, the distal member of the implant maintains a constant rotational position, while moving distally. That is, as the implant body rotates and engages with bone, the distal member does not rotate but moves distally as the implant body is advanced.

As the grip 210 is rotated, the threads 223 on the threaded driver 222 engage with the projections 214 on the driving portion 212 such that the implant actuator 206 moves distally relative to the driving portion 212 to distally advance the implant. The user can distally advance the implant into the bore at least until a proximal end of the implant is flush with a surface of the bone. Once fully implanted, the user can manipulate the wire actuator 205 proximally with respect to the implant actuator 206 to withdraw the wire 32 into the inner shaft, thereby opening the loop and freeing the sutures from the implant delivery device 200. Once the loop has been opened the implant delivery device 200 can be withdrawn without catching on the sutures.

As discussed herein, the implant delivery device 200 can be used to perform method 1300 and implant the implant 20 as shown in FIGS. 12A-12F while using the implant delivery device 200 instead of implant delivery device 40. The implant delivery device 200 provides a device that has the wire actuator 205 located proximal to the implant actuator 206 and proximally to the grip 210 that is used to rotate the implant during insertion.

Various Notes & Examples

Each of the following non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the fall scope of equivalents to which such claims are entitled.

What is claimed:

1. An anchoring system, comprising:
    an implant delivery device, including:
        a handle, including:
            an implant actuator handle portion including a grip, a driving portion, a ratchet portion, and a tip, wherein an actuating ratchet including a plurality of grooves is positioned within the ratchet portion; and
            a wire actuator handle portion including an inner surface defining a bore and a plurality of flexible arms extending from the inner surface toward a longitudinal axis of the wire actuator handle portion,
        wherein a number of the flexible arms are configured to engage the grooves of the ratchet portion as the implant actuator handle portion is rotated, the number of flexible arms is less than a total number of the plurality of flexible arms.

2. The anchoring system claim 1, wherein the wire actuator handle portion is positioned distal to the grip.

3. The anchoring system in claim 1, wherein the implant delivery device includes a distal end that is convertible from an open configuration to a closed configuration.

4. The anchoring system in claim 3, wherein the wire actuator handle portion is configured to transition the distal end from the closed configuration to the open configuration by moving the wire actuator handle portion proximally relative to the implant actuator handle portion.

5. The anchoring system in claim 1, wherein the implant delivery device further includes:
    a cannulated outer shaft non-rotationally coupled to the implant actuating handle portion.

6. The anchoring system in claim 5, further including:
    a cannulated implant non-rotationally coupled to a distal end of the cannulated outer shaft.

7. The anchoring system of claim 6, wherein, when a rotational force is applied to the grip, the rotational force is translated to the cannulated implant via the cannulated outer shaft.

8. The anchoring system of claim 7, wherein when the rotational force is applied to the grip, the implant actuating handle portion rotates relative to the wire actuating handle portion.

9. An anchoring system, comprising:
    an implant delivery device, including:
        a cannulated outer shaft;
        an inner shaft slidably received in the cannulated outer shaft,
        a projection extending distally beyond a distal end of the inner shaft;

a wire translatable through the inner shaft from a retracted position to an extended position, the extended position including a distal end of the wire extending a distance beyond the distal end of the inner shaft such that the wire and the projection form a closed loop for trapping a suture; and a handle, including:
a wire actuator handle portion configured to controllably translate the wire from the extended position to the retracted position; and
an implant actuator handle portion including a grip that is configured to controllably rotate the cannulated outer shaft, the grip positioned proximal to the wire actuator handle portion.

10. The anchoring system of claim 9, wherein the wire actuator handle portion includes an inner surface defining a bore and a plurality of flexible arms extending from the inner surface toward a longitudinal axis of the wire actuator portion.

11. The anchoring system of claim 10, wherein the implant delivery device further includes an actuating ratchet positioned within a ratchet portion of the implant actuator handle portion, the actuating ratchet including a plurality of grooves.

12. The anchoring system of claim 11, wherein the wire actuator handle portion is positioned around the ratchet portion of the implant actuator handle portion.

13. The anchoring system of claim 12, wherein the plurality of flexible arms are configured to engage a respective groove of the actuating ratchet.

14. The anchoring system of claim 13, wherein as the grip is rotated, the ratchet portion rotates within and relative to the wire actuating handle portion.

15. The anchoring system of claim 13, wherein, as the grip is rotated within the wire actuating handle portion, the plurality of flexible arms are configured such that less than all of the plurality of flexible arms engage the actuating ratchet.

16. The anchoring system of claim 9, wherein the wire actuator handle portion is configured to move proximally relative to the implant actuator handle portion to retract the wire and transition the closed loop to an open loop.

17. The anchoring system of claim 9, wherein the implant actuator handle portion is configured to rotate relative to the wire actuator handle portion to move a cannulated implant coupled to the cannulated outer shaft distally relative to the wire actuator handle portion.

18. A method for securing a suture to a pre-drilled bore, the method comprising:
providing an implant delivery device including a distal end and a handle portion, wherein the distal end is convertible from an open configuration to a closed configuration, and the handle includes:
an implant actuator handle portion including a grip that is configured to controllably rotate an implant body;
a wire actuator handle portion positioned around a portion of the implant actuator handle portion such that the wire actuator handle portion is positioned distal to the implant actuator handle portion, the wire actuator handle portion configured to controllably transition the distal end of the implant delivery device from a closed configuration to an open configuration;
positioning the distal end of the implant delivery device, in the open configuration, proximate the suture;
converting the distal end of the implant delivery device from the open configuration to the closed configuration to encircle the suture in an eyelet of the closed configuration, the suture being slidable through the eyelet when the distal end is in the closed configuration;
inserting the distal end of the implant delivery device into pre-drilled bore;
deploying a cannulated implant, having a threaded outer surface, from the implant delivery device into the pre-drilled bore, the cannulated implant securing the suture between the threaded outer surface and a wall of the pre-drilled bore when the cannulated implant is deployed; and
converting the distal end of the implant delivery device from the closed configuration to the open configuration; and
retracting the implant delivery device from the pre-drilled bore.

19. The method of claim 18, wherein deploying the cannulated implant comprises:
controllably rotating the cannulated implant about a longitudinal implant axis of the cannulated implant.

20. The method of claim 18, wherein controllably rotating the cannulated implant about a longitudinal implant axis of the cannulated implant includes:
imparting a rotation to the grip of the implant actuating handle portion that translates the rotation to a cannulated outer shaft of the implant delivery device and to the cannulated implant that is non-rotationally coupled to a distal end of the cannulated outer shaft; and
wherein converting the distal end of the implant delivery device from the closed configuration to the open configuration includes:
controllably moving the wire actuator handle portion proximally relative to the implant actuating device to retract a portion of a wire into the inner shaft.

* * * * *

UNITED STATES PATENT AND TRADEMARK OFFICE
CERTIFICATE OF CORRECTION

PATENT NO. : 11,026,674 B2
APPLICATION NO. : 16/414352
DATED : June 8, 2021
INVENTOR(S) : Norton et al.

Page 1 of 1

It is certified that error appears in the above-identified patent and that said Letters Patent is hereby corrected as shown below:

In the Claims

In Column 20, Line 36, in Claim 2, after "system", insert --in--

In Column 22, Line 20, in Claim 18, after "into", insert --the--

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*